(12) United States Patent
Jeanguenat et al.

(10) Patent No.: US 9,403,845 B2
(45) Date of Patent: Aug. 2, 2016

(54) PESTICIDALLY ACTIVE PYRIDYL- AND PYRIMIDYL- SUBSTITUTED PYRAZOLE DERIVATIVES

(71) Applicant: Syngenta Participations AG, Basel (CH)

(72) Inventors: Andre Jeanguenat, Stein (CH); Aurelien Bigot, Stein (CH); Andrew Edmunds, Stein (CH); Roger Graham Hall, Stein (CH); Sebastian Rendler, Stein (CH); Didier Zurwerra, Stein (CH)

(73) Assignee: Syngenta Participations AG, Basel (CH)

( * ) Notice: Subject to any disclaimer, the term of this patent is extended or adjusted under 35 U.S.C. 154(b) by 20 days.

(21) Appl. No.: 14/421,556

(22) PCT Filed: Aug. 15, 2013

(86) PCT No.: PCT/EP2013/067066
§ 371 (c)(1),
(2) Date: Feb. 13, 2015

(87) PCT Pub. No.: WO2014/029684
PCT Pub. Date: Feb. 27, 2014

(65) Prior Publication Data
US 2015/0232482 A1    Aug. 20, 2015

(30) Foreign Application Priority Data

Aug. 20, 2012 (EP) ..................... 12181007

(51) Int. Cl.
| | |
|---|---|
| *C07D 513/04* | (2006.01) |
| *C07D 401/14* | (2006.01) |
| *C07D 471/04* | (2006.01) |
| *C07D 491/052* | (2006.01) |
| *C07D 417/14* | (2006.01) |
| *C07D 413/14* | (2006.01) |
| *C07D 498/04* | (2006.01) |
| *A01N 43/42* | (2006.01) |
| *A01N 43/60* | (2006.01) |
| *A01N 43/707* | (2006.01) |
| *A01N 43/76* | (2006.01) |
| *A01N 43/90* | (2006.01) |
| *A01N 51/00* | (2006.01) |
| *A01N 43/78* | (2006.01) |

(52) U.S. Cl.
CPC .............. *C07D 513/04* (2013.01); *A01N 43/42* (2013.01); *A01N 43/60* (2013.01); *A01N 43/707* (2013.01); *A01N 43/76* (2013.01); *A01N 43/78* (2013.01); *A01N 43/90* (2013.01); *A01N 51/00* (2013.01); *C07D 401/14* (2013.01); *C07D 413/14* (2013.01); *C07D 417/14* (2013.01); *C07D 471/04* (2013.01); *C07D 491/052* (2013.01); *C07D 498/04* (2013.01)

(58) Field of Classification Search
CPC .. C07D 513/04; C07D 401/14; C07D 413/14; C07D 417/14; C07D 471/04; C07D 491/052; C07D 498/04; A01N 43/42; A01N 43/60; A01N 43/707; A01N 43/76; A01N 43/78; A01N 43/90; A01N 51/00
See application file for complete search history.

(56) References Cited

U.S. PATENT DOCUMENTS 9,133,218 B2 *   9/2015   Chen .................. A01N 43/78

FOREIGN PATENT DOCUMENTS

| WO | 2011045224 | 4/2011 | |
|---|---|---|---|
| WO | WO2011045224 A1 * | 4/2011 | ............. A01N 43/56 |

OTHER PUBLICATIONS

International Search Report for International Patent Application No. PCT/EP2013/067066 mailed Sep. 30, 2013.
European Search Report for EP Patent Application No. 12181007.1 mailed Jan. 30, 2013.

* cited by examiner

*Primary Examiner* — Jane C Oswecki
(74) *Attorney, Agent, or Firm* — R. Kody Jones

(57) ABSTRACT

Compounds of formula (I) wherein the substituents are as defined in claim 1, and the agrochemically acceptable salts and all stereoisomers and tautomeric forms of the compounds of formula I can be used as insecticides and can be prepared in a manner known per se.

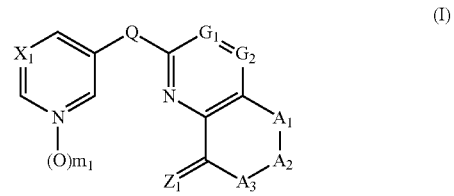

(I)

13 Claims, No Drawings

PESTICIDALLY ACTIVE PYRIDYL- AND PYRIMIDYL- SUBSTITUTED PYRAZOLE DERIVATIVES

RELATED APPLICATION INFORMATION

This application is a 371 of International Application No. PCT/EP2013/067066, filed 15 Aug. 2013, which claims priority to EP Patent Application No. 12181007.1, filed 20 Aug. 2012, the contents of which are incorporated herein by reference.

The present invention relates to insecticidally active pyridyl- and pyrimidyl- substituted pyrazole derivatives to processes for their preparation, to compositions comprising those compounds, and to their use for controlling insects or representatives of the order Acarina.

1-(3-Pyridyl)-pyrazole derivatives with pesticidal action are known and described, for example, in WO 2011/045224, WO 2011/045240, WO 2012/000896 and WO 2012/061290.

There have now been found novel pyridyl- and pyrimidyl- substituted pyrazole derivatives with pesticidal properties.

The present invention accordingly relates to compounds of formula I,

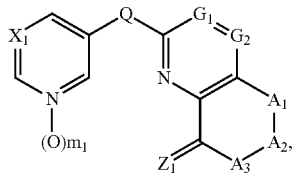

(I)

wherein
$X_1$ is nitrogen or $CR_1$;
$G_1$ is nitrogen or $CR_2$;
$G_2$ is nitrogen or $CR_3$;
or $G_1$-$G_2$ together is —S—, —O—, —NH—, or N—$CH_3$;
$A_1$ is oxygen, $S(O)n_1$, $S(O)(=NR_4)$, C=O, $NR_5$, $CR_6R_7$, —$CR_8CR_9$— or a direct bond;
$A_2$ is oxygen, $S(O)n_2$, $NR_{10}$, C=O or $CR_{11}R_{12}$;
$A_3$ is oxygen, $NR_{13}$, $CR_{14}R_{15}$ or —$CR_{16}CR_{17}$—;
or $A_2$-$A_3$ together represents a group —$CR_{18}$=$CR_{19}$—;
with the provisos that;
  a) not more than 1 substituent A can be oxygen or sulfur;
  b) not more than 2 substituents A can be nitrogen;
  c) 2 substituents A as nitrogen can be adjacent to each other or separated by a sulfur or carbon substituent;
$R_1$ is hydrogen or halogen;
$R_2$ and $R_3$, independently from each other, are hydrogen, halogen, $C_1$-$C_3$alkyl or $C_1$-$C_3$haloalkyl;
$R_4$, $R_5$, $R_{10}$ and $R_{13}$, independently from each other, are hydrogen, cyano, $C_1$-$C_2$alkyl, $C_3$-$C_6$cycloalkyl, $C_1$-$C_2$haloalkyl, $C(O)C_1$-$C_3$alkyl, $(CO)OC_1$-$C_3$alkyl, $SO_2NHC_1$-$C_3$alkyl, $SO_2N(C_1$-$C_3$alkyl), $SO_2C_1$-$C_3$alkyl, $SO_2$-phenyl, wherein the said phenyl can be mono- or polysubstituted on the phenyl ring by substituents selected from the group consisting of $C_1$-$C_3$alkyl, $C_1$-$C_3$haloalkyl, $C_1$-$C_3$alkoxy, $C_1$-$C_3$haloalkoxy, halogen, cyano and nitro;
$R_6$, $R_7$, $R_8$, $R_9$, $R_{11}$, $R_{12}$, $R_{14}$, $R_{15}$, $R_{16}$ and $R_{17}$, independently from each other, are hydrogen, halogen, nitro, cyano, hydroxy, CHO, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_4$alkoxy, $C_1$-$C_4$alkoxy-$C_1$-$C_4$alkoxy-$C_1$-$C_4$alkyl, $C_1$-$C_4$haloalkoxy, $C_1$-$C_4$alkylthio, $C_1$-$C_4$haloalkylthio, $C_1$-$C_4$haloalkylsulfinyl, $C_1$-$C_4$haloalkylsulfonyl, $C_1$-$C_4$alkylsulfinyl, $C_1$-$C_4$alkylsulfonyl, $C_1$-$C_4$alkylsulfonyl-$C_1$-$C_4$alkyl, $C_1$-$C_4$alkylsulfoximino-$C_1$-$C_4$alkyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, $C_1$-$C_4$alkoxyimino-$C_1$-$C_4$alkyl, —$CONHSO_2$—$C_1$-$C_6$-alkyl, —$CONHSO_2N(C_1$-$C_6$-alkyl$)_2$, or are a three- to ten-membered, monocyclic or fused bicyclic ring system which may be aromatic, partially saturated or fully saturated, said three- to ten-membered, monocyclic or fused bicyclic ring system can be substituted by one to three substituents independently selected from the group consisting of $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_2$-$C_4$haloalkenyl, $C_2$-$C_4$haloalkynyl, $C_3$-$C_6$halocycloalkyl, halogen, cyano, nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_1$-$C_4$alkylamino, $C_2$-$C_6$dialkylamino, $C_3$-$C_6$cycloalkylamino, $C_1$-$C_4$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, and $C_2$-$C_8$ dialkylaminocarbonyl;
$R_{18}$ and $R_{19}$, independently from each other, are hydrogen, halogen, nitro, cyano, hydroxy, CHO, $C_1$-$C_6$alkyl, $C_2$-$C_6$alkenyl, $C_2$-$C_6$alkynyl, $C_1$-$C_6$alkoxy, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_4$alkylsulfonyl, $C_1$-$C_4$alkylsulfonyl-$C_1$-$C_4$alkyl, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, $C_1$-$C_4$alkoxyimino-$C_1$-$C_4$alkyl, —$CONHSO_2$—$C_1$-$C_6$-alkyl, —$CONHSO_2N(C_1$-$C_6$-alkyl$)_2$, or are a three- to ten-membered, monocyclic or fused bicyclic ring system which may be aromatic, partially saturated or fully saturated, said three- to ten-membered, monocyclic or fused bicyclic ring system can be substituted by one to three substituents independently selected from the group consisting of $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_2$-$C_4$haloalkenyl, $C_2$-$C_4$haloalkynyl, $C_3$-$C_6$halocycloalkyl, halogen, cyano, nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_1$-$C_4$alkylamino, $C_2$-$C_6$dialkylamino, $C_3$-$C_6$cycloalkylamino, $C_1$-$C_4$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, and $C_2$-$C_8$ dialkylaminocarbonyl;
$Z_1$ is oxygen, $NOR_{20}$, $NR_{21}$, N—$NR_{22}R_{23}$, or N—$N(R_{24})SO_2(R_{25})$,
$R_{20}$, $R_{21}$, $R_{22}$ and $R_{25}$ independently from each other, are hydrogen, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, —$CONHSO_2$—$C_1$-$C_6$-alkyl, —$CONHSO_2N(C_1$-$C_6$-alkyl$)_2$ or are a five- to ten-membered monocyclic or fused bicyclic ring system which may be aromatic, saturated or partially saturated and may contain 1 to 4 heteroatoms selected from the group consisting of nitrogen, oxygen and sulfur, where the ring system is attached directly or via a $C_1$-$C_4$alkylene, $C_2$-$C_4$alkenyl-$C_1$-$C_4$alkylene, $C_2$-$C_4$alkynyl-$C_1$-$C_4$alkylene, —NH—$C_1$-$C_4$alkylene, —N($C_1$-$C_4$alkyl)$C_1$-$C_4$alkylene, SO—$C_1$-$C_4$alkylene, SO—$C_1$-$C_4$alkylene, —SO$_2$—$C_1$-$C_4$alkylene or O—$C_1$-$C_4$alkylene group to the heteroatom substituent, and where each ring system may not contain more than two oxygen atoms and not more than two sulfur atoms and the ring system for its part may be mono-, di- or trisubstituted by $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, hydroxyl, $C_1$-$C_6$haloalkoxy, $C_3$-$C_6$alkenyloxy, $C_3$-$C_6$alkynyloxy, mercapto, $C_1$-$C_6$alkylthio, $C_1$-$C_6$haloalkylthio, $C_3$-$C_6$alkenylthio, $C_3$-$C_6$haloalkenylthio, $C_3$-$C_6$alkynylthio, $C_2$-$C_5$alkoxyalkylthio, $C_3$-$C_5$acetylalkylthio, $C_3$-$C_6$alkoxycarbonylalkylthio, $C_2$-$C_4$cyanoalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_2$alkylaminosulfonyl, di($C_1$-$C_2$alkyl)aminosulfonyl, di($C_1$-$C_4$alkyl)amino, halogen, cyano, nitro, phenyl and benzylthio, said phenyl and benzylthio can be mono- or polysubstituted on the phenyl ring by substituents selected from the group consisting of $C_1$-$C_3$alkyl, $C_1$-$C_3$haloalkyl, $C_1$-$C_3$alkoxy, $C_1$-$C_3$haloalkoxy, halogen, cyano and nitro, and where the substituents on the nitrogen in the heterocyclic ring are different from halogen;

$R_{23}$ and $R_{24}$ are hydrogen or $C_1$-$C_3$alkyl;

Q is a ring system $Q_1$

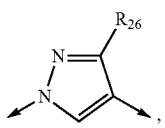

(Q$_1$)

wherein $R_{26}$ is hydrogen, $C_1$-$C_4$alkyl, halogen, $C_1$-$C_4$haloalkyl, cyano, $C_1$-$C_4$alkoxy, hydroxyl, amino, $C_1$-$C_4$alkylamino, di-($C_1$-$C_4$alkyl)amino, $C_1$-$C_4$alkylthio or nitro;

or $R_{26}$ is a three- to four-membered ring system which can be partially saturated or fully saturated and can contain one heteroatom selected form the group consisting of nitrogen, oxygen and sulfur; said three- to four-membered ring system can be mono- to polysubstituted by substituents independently selected from the group consisting of halogen, methyl and trifluoromethyl;

or $R_{26}$ is $C_2$-$C_6$alkenyl which can be mono- to polysubstituted by substituents independently selected from the group consisting of halogen, methyl and trifluoromethyl;

or $R_{26}$ is $C_2$-$C_6$alkynyl which can be substituted by substituents selected from the group consisting of halogen, methyl and $C_1$-$C_2$haloalkyl;

$m_1$ is 0 or 1; and $n_1$ and $n_2$, independently from each other, are 0, 1 or 2; and agrochemically acceptable salts/enantiomers/tautomers/N-oxides of those compounds.

Compounds of formula I which have at least one basic centre can form, for example, acid addition salts, for example with strong inorganic acids such as mineral acids, for example perchloric acid, sulfuric acid, nitric acid, nitrose acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-loweralkylamine, for example ethyl-, diethyl-, triethyl- or dimethylpropylamine, or a mono-, di- or trihydroxy-lower-alkylamine, for example mono-, di- or triethanolamine.

The alkyl groups occurring in the definitions of the substituents can be straight-chain or branched and are, for example, methyl, ethyl, n-propyl, isopropyl, n-butyl, sec-butyl, iso-butyl, tert-butyl, pentyl, hexyl, nonyl, decyl and their branched isomers. Alkoxy, alkenyl and alkynyl radicals are derived from the alkyl radicals mentioned. The alkenyl and alkynyl groups can be mono- or polyunsaturated.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

Alkoxy groups preferably have a preferred chain length of from 1 to 6 carbon atoms. Alkoxy is, for example, methoxy, ethoxy, propoxy, i-propoxy, n-butoxy, isobutoxy, sec-butoxy and tert-butoxy and also the isomeric pentyloxy and hexyloxy radicals; preferably methoxy and ethoxy.

Alkoxycarbonyl is, for example, methoxycarbonyl, ethoxycarbonyl, propoxycarbonyl, isopropoxycarbonyl, n-butoxycarbonyl, isobutoxycarbonyl, sec-butoxycarbonyl or tert-butoxycarbonyl; preferably methoxycarbonyl or ethoxycarbonyl. Haloalkoxy groups preferably have a chain length of from 1 to 6 carbon atoms. Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy.

Alkylthio groups preferably have a chain length of from 1 to 6 carbon atoms. Alkylthio is, for example, methylthio, ethylthio, propylthio, isopropylthio, n-butylthio, isobutylthio, sec-butylthio or tert-butylthio, preferably methylthio and ethylthio. Alkylsulfinyl is, for example, methylsulfinyl, ethylsulfinyl, propylsulfinyl, isopropylsulfinyl, n-butylsulfinyl, isobutylsulfinyl, sec-butylsulfinyl, tert-butylsulfinyl; preferably methylsulfinyl and ethylsulfinyl.

Alkylsulfonyl is, for example, methylsulfonyl, ethylsulfonyl, propylsulfonyl, isopropylsulfonyl, n-butylsulfonyl, isobutylsulfonyl, sec-butylsulfonyl or tert-butylsulfonyl; preferably methylsulfonyl or ethylsulfonyl.

Alkylamino is, for example, methylamino, ethylamino, n-propylamino, isopropylamino or the isomeric butylamines. Dialkylamino is, for example, dimethylamino, methylethylamino, diethylamino, n-propylmethylamino, dibutylamino and diisopropylamino. Preference is given to alkylamino groups having a chain length of from 1 to 4 carbon atoms.

Alkoxyalkyl groups preferably have a chain length of 1 to 6 carbon atoms.

Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

The cycloalkyl groups preferably have from 3 to 6 ring carbon atoms, for example cyclopropyl, cyclobutyl, cyclopentyl and cyclohexyl. Phenyl, also as part of a substituent such as phenoxy, benzyl, benzyloxy, benzoyl, phenylthio, phenylalkyl, phenoxyalkyl, may be substituted. In this case, the substituents can be in ortho, meta and/or para position. The preferred substituent positions are the ortho and para positions to the ring attachment point.

In the context of this invention, with regard to the definition of a ring system, the definition "where the ring system is attached directly or via a $C_1$-$C_4$alkylene, $C_2$-$C_4$alkenyl-$C_1$-$C_4$alkylene, $C_2$-$C_4$alkynyl-$C_1$-$C_4$alkylene, —NH—$C_1$-$C_4$alkylene, —N($C_1$-$C_4$alkyl)$C_1$-$C_4$alkylene, SO—$C_1$-$C_4$alkylene, SO—$C_1$-$C_4$alkylene, —$SO_2$—$C_1$-$C_4$alkylene or O—$C_1$-$C_4$alkylene group to the heteroatom substituent," the attachment of the ring system is on the left side of said definition, for example the group $NOR_{20}$ for the substituent $Z_1$ can be N—O—$CH_2$—$CH_2$—NH-pyridyl.

In the context of this invention "mono- to polysubstituted" in the definition of the substituents, means typically, depending on the chemical structure of the substituents, monosubstituted to seven-times substituted, preferably monosubstituted to five-times substituted, more preferably mono-, double- or triple-substituted.

In the context of this invention "halo-substituted phenyl" in the definition of the substituents, means for example a phenyl group which is mono- to polysubstituted by substituents selected from the group consisting of fluoro, chloro, bromo and iodo. Preferably "halo-substituted phenyl" is phenyl which is mono-di or tri-substituted by chloro, in particular mono-substituted by chloro.

According to this invention, a three- to four membered, a three- to ten-membered or a five- to ten-membered monocyclic or fused bicyclic ring system which may be aromatic, partially saturated or fully saturated; said ring system can contain 1 to 4 hetero atoms selected from the group consisting of nitrogen, oxygen and sulfur, it not being possible for each ring system to contain more than 2 oxygen atoms and more than 2 sulfur atoms; is, depending of the number of ring members, for example, selected from the group consisting of

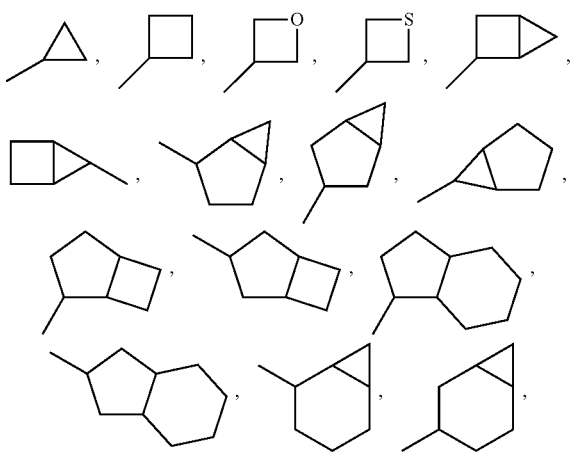

cyclopentyl, cyclohexyl, where said cycloalkylgroups for their part may be preferably unsubstituted or substituted by $C_1$-$C_6$alkyl or halogen, or is phenyl, benzyl, naphthyl or the following heterocyclic groups: pyrrolyl; pyridyl; pyrazolyl; pyrimidyl; pyrazinyl; imidazolyl; thiadiazolyl; quinazolinyl; furyl; oxadiazolyl; indolizinyl; pyranyl; isobenzofuranyl; thienyl; naphthyridinyl; (1-methyl-1H-pyrazol-3-yl)-; (1-ethyl-1H-pyrazol-3-yl)-; (1-propyl-1H-pyrazol-3-yl)-; (1H-pyrazol-3-yl)-; (1,5-dimethyl-1H-pyrazol-3-yl)-; (4-chloro-1-methyl-1H-pyrazol-3-yl)-; (1H-pyrazol-1-yl)-; (3-methyl-1H-pyrazol-1-yl)-; (3,5-dimethyl-1H-pyrazol-1-yl)-; (3-isoxazolyl)-; (5-methyl-3-isoxazolyl)-; (3-methyl-5-isoxazolyl)-; (5-isoxazolyl)-; (1H-pyrrol-2-yl)-; (1-methyl-1H-pyrrol-2-yl)-; (1H-pyrrol-1-yl)-; (1-methyl-1H-pyrrol-3-yl)-; (2-furanyl)-; (5-methyl-2-furanyl)-; (3-furanyl)-; (5-methyl-2-thienyl)-; (2-thienyl)-; (3-thienyl)-; (1-methyl-1H-imidazol-2-yl)-; (1H-imidazol-2-yl)-; (1-methyl-1H-imidazol-4-yl)-; (1-methyl-1H-imidazol-5-yl)-; (4-methyl-2-oxazolyl)-; (5-methyl-2-oxazolyl)-; (2-oxazolyl)-; (2-methyl-5-oxazolyl)-; (2-methyl-4-oxazolyl)-; (4-methyl-2-thiazolyl)-; (5-methyl-2-thiazolyl)-; (2-thiazolyl)-; (2-methyl-5-thiazolyl)-; (2-methyl-4-thiazolyl)-; (3-methyl-4-isothiazolyl)-; (3-methyl-5-isothiazolyl)-; (5-methyl-3-isothiazolyl)-; (1-methyl-1H-1,2,3-triazol-4-yl)-; (2-methyl-2H-1,2,3-triazol-4-yl)-; (4-methyl-2H-1,2,3-triazol-2-yl)-; (1-methyl-1H-1,2,4-triazol-3-yl)-; (1,5-dimethyl-1H-1,2,4-triazol-3-yl)-; (3-methyl-1H-1,2,4-triazol-1-yl)-; (5-methyl-1H-1,2,4-triazol-1-yl)-; (4,5-dimethyl-4H-1,2,4-triazol-3-yl)-; (4-methyl-4H-1,2,4-triazol-3-yl)-; (4H-1,2,4-triazol-4-yl)-; (5-methyl-1,2,3-oxadiazol-4-yl)-; (1,2,3-oxadiazol-4-yl)-; (3-methyl-1,2,4-oxadiazol-5-yl)-; (5-methyl-1,2,4-oxadiazol-3-yl)-; (4-methyl-3-furazanyl)-; (3-furazanyl)-; (5-methyl-1,2,4-oxadiazol-2-yl)-; (5-methyl-1,2,3-thiadiazol-4-yl)-; (1,2,3-thiadiazol-4-yl)-; (3-methyl-1,2,4-thiadiazol-5-yl)-; (5-methyl-1,2,4-thiadiazol-3-yl)-; (4-methyl-1,2,5-thiadiazol-3-yl)-; (5-methyl-1,3,4-thiadiazol-2-yl)-; (1-methyl-1H-tetrazol-5-yl)-; (1H-tetrazol-5-yl)-; (5-methyl-1H-tetrazol-1-yl)-; (2-methyl-2H-tetrazol-5-yl)-; (2-ethyl-2H-tetrazol-5-yl)-; (5-methyl-2H-tetrazol-2-yl)-; (2H-tetrazol-2-yl)-; (2-pyridyl)-; (6-methyl-2-pyridyl)-; (4-pyridyl)-; (3-pyridyl)-; (6-methyl-3-pyridazinyl)-; (5-methyl-3-pyridazinyl)-; (3-pyridazinyl)-; (4,6-dimethyl-2-pyrimidinyl)-; (4-methyl-2-pyrimidinyl)-; (2-pyrimidinyl)-; (2-methyl-4-pyrimidinyl)-; (2-chloro-4-pyrimidinyl)-; (2,6-dimethyl-4-pyrimidinyl)-; (4-pyrimidinyl)-; (2-methyl-5-pyrimidinyl)-; (6-methyl-2-pyrazinyl)-; (2-pyrazinyl)-; (4,6-dimethyl-1,3,5-triazin-2-yl)-; (4,6-dichloro-1,3,5-triazin-2-yl)-; (1,3,5-triazin-2-yl)-; (4-methyl-1,3,5-triazin-2-yl)-; (3-methyl-1,2,4-triazin-5-yl)-; (3-methyl-1,2,4-triazin-6-yl)-;

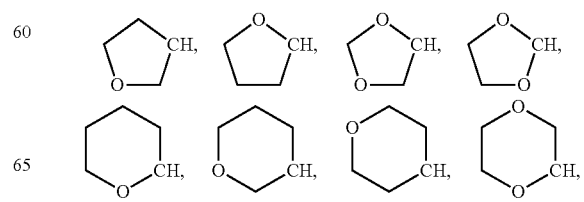

-continued

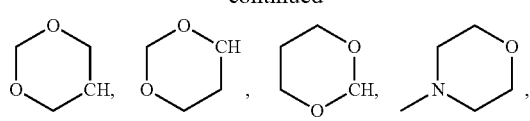

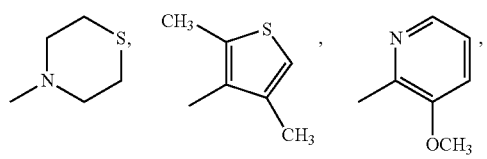

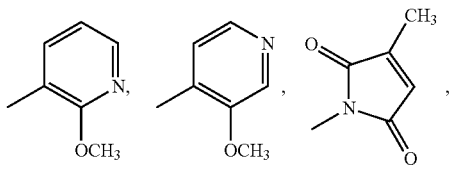

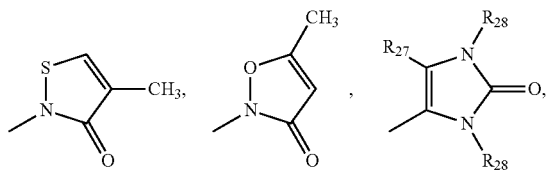

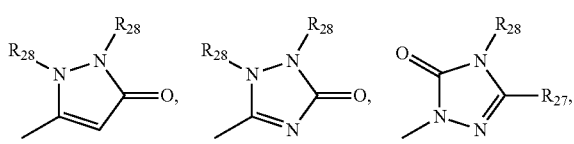

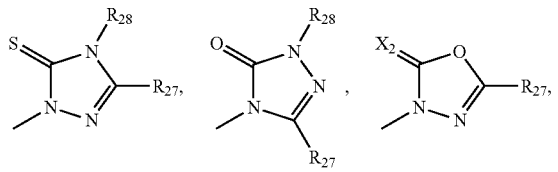

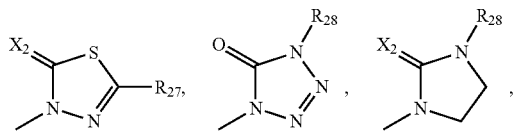

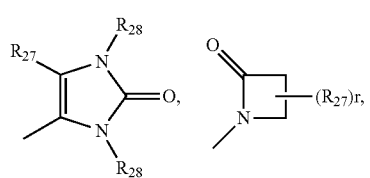

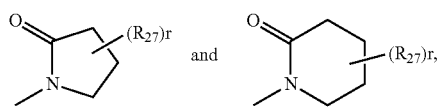

wherein each $R_{28}$ is hydrogen or methyl and each $R_{27}$ is hydrogen, $C_1$-$C_3$alkyl, $C_1$-$C_3$alkoxy, $C_1$-$C_3$alkylthio or trifluoromethyl, $X_2$ is oxygen or sulfur and r=1, 2, 3 or 4.

Where no free valency is indicated in those definitions, for example as in

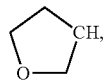

the linkage site is located at the carbon atom labelled "CH" or in a case such as, for example,

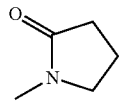

at the bonding site indicated at the bottom left.

Preferably $A_2$ is oxygen, $S(O)n_2$, $NR_{10}$ or $CR_{11}R_{12}$.

In preferred compounds of formula I,
$X_1$ is CH or C—F;
$A_1$ is oxygen, $S(O)n_1$, C═O, $NR_5$, $CR_6R_7$, —$CR_8CR_9$— or a direct bond;
$A_2$ is $CR_{11}R_{12}$; and
$A_3$ is $CR_{14}R_{15}$ or —$CR_{16}CR_{17}$—.

In further preferred compounds of formula I,
$X_1$ is CH or C—F;
$G_1$ is $CR_2$;
$G_2$ is $CR_3$; or
$G_1$-$G_2$ together is —S—, —O—;
$A_1$ is oxygen, $S(O)n_1$, C═O, $NR_5$, $CR_6R_7$, —$CR_8CR_9$— or a direct bond;
$A_2$ is $CR_{11}R_{12}$; and
$A_3$ is $CR_{14}R_{15}$ or —$CR_{16}CR_{17}$—.

In further preferred compounds of formula I,
$X_1$ is CH;
$G_1$ is CH;
$G_2$ is CH; or
$G_1$-$G_2$ together is —S—;
$A_1$ is oxygen, $S(O)n_1$, C═O, $NR_5$, $CR_6R_7$, —$CR_8CR_9$— or a direct bond;
$A_2$ is $CR_{11}R_{12}$; and
$A_3$ is $CR_{14}R_{15}$ or —$CR_{16}CR_{17}$—.

In further preferred compounds of formula I,
$X_1$ is CH;
$G_1$ is CH;
$G_2$ is CH; or
$G_1$-$G_2$ together is —S—;
$A_1$ is oxygen, $S(O)n_1$, C═O, $NR_5$, $CR_6R_7$, —$CR_8CR_9$— or a direct bond;
$A_2$ is $CR_{11}R_{12}$;
$A_3$ is $CR_{14}R_{15}$ or —$CR_{16}CR_{17}$—; and
$Z_1$ is $NOR_{20}$, N—$NR_{22}R_{23}$, or N—$N(R_{24})SO_2(R_{25})$.

In further preferred compounds of formula I,
$X_1$ is CH;
$G_1$ is CH;
$G_2$ is CH; or
$G_1$-$G_2$ together is —S—;
$A_1$ is oxygen, $S(O)n_1$, C═O, $NR_5$, $CR_6R_7$, —$CR_8CR_9$— or a direct bond;
$A_2$ is $CH_2$;
$A_3$ is $CH_2$ or —$CH_2CH_2$—; and
$Z_1$ is $NOR_{20}$, N—$NR_{22}R_{23}$, or N—$N(R_{24})SO_2(R_{25})$.

In further preferred compounds of formula I,
$X_1$ is CH;
$G_1$ is CH;
$G_2$ is CH;
$A_1$ is oxygen, $S(O)n_1$, C=O, $NR_5$, $CH_2$, —$CH_2CH_2$— or a direct bond;
$A_2$ is $CH_2$;
$A_3$ is $CH_2$ or —$CH_2CH_2$—; and
$Z_1$ is $NOR_{20}$, N—$NR_{22}R_{23}$, or N—$N(R_{24})SO_2(R_{25})$.

In further preferred compounds of formula I,
$X_1$ is CH;
$G_1$ is CH;
$G_2$ is CH; or
$G_1$-$G_2$ together is —S—;
$A_1$ is oxygen, $S(O)n_1$, C=O, $NR_5$, $CH_2$, —$CH_2CH_2$— or a direct bond;
$A_2$ is $CH_2$;
$A_3$ is $CH_2$; and
$Z_1$ is $NOR_{20}$.

In further preferred compounds of formula I,
$X_1$ is CH;
$G_1$ is CH;
$G_2$ is CH;
$A_1$ is oxygen, $S(O)n_1$, $NR_5$, $CH_2$ or a direct bond;
$A_2$ is $CH_2$;
$A_3$ is $CH_2$;
and
$Z_1$ is $NOR_{20}$, N—$NR_{22}R_{23}$, or N—$N(R_{24})SO_2(R_{25})$.

In all of the above-mentioned preferred embodiments of the invention,
$R_{26}$ is hydrogen, $C_1$-$C_4$alkyl, halogen, $C_1$-$C_4$haloalkyl, cyano, $C_1$-$C_4$alkoxy, hydroxyl, amino, $C_1$-$C_4$alkylamino, di-($C_1$-$C_4$alkyl)amino, $C_1$-$C_4$alkylthio or nitro; more preferably $R_{26}$ is hydrogen, $C_1$-$C_4$alkyl, halogen, $C_1$-$C_4$haloalkyl, cyano, $C_1$-$C_4$alkoxy, hydroxyl; and most preferably $R_{26}$ is hydrogen, $C_1$-$C_4$alkyl or halogen.

If in all of the above-mentioned preferred embodiments of the invention, $R_{26}$ is hydrogen, $C_1$-$C_4$alkyl or halogen, then $Z_1$ is preferably oxygen, $NOR_{20}$, or N—$NR_{22}R_{23}$, wherein $R_{20}$ is $C_1$-$C_6$alkyl or $C_2$-$C_6$alkenyl; $R_{21}$ is hydrogen or $C_1$-$C_4$alkyl; and $R_{22}$ is $C_1$-$C_6$alkyl or $C_1$-$C_6$alkylcarbonyl.

Preferred compounds of formula I are represented by the compounds of formula Iaa

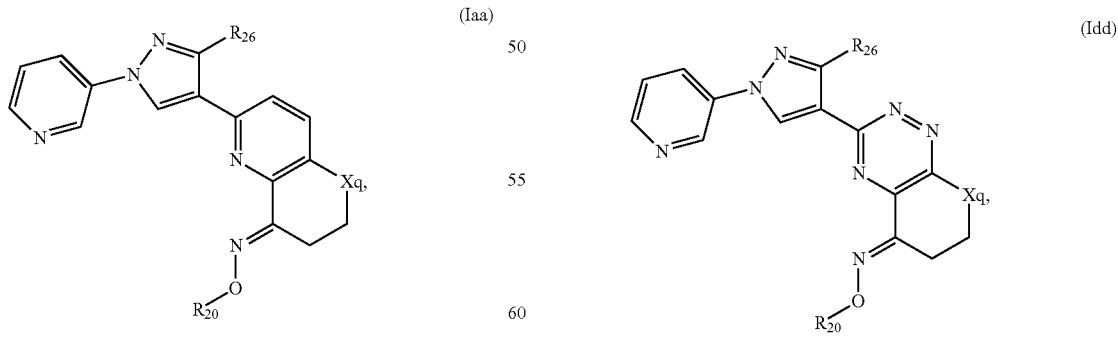

(Iaa)

wherein
$R_{20}$ is hydrogen, $C_1$-$C_6$alkyl or $C_2$-$C_6$alkenyl;
$R_{26}$ is hydrogen or $C_1$-$C_6$alkyl, and
Xq is oxygen, —$CH_2$—, —N($C_1$-$C_6$alkyl)- or —N($C_1$-$C_6$alkylsulfonyl)-.

Further preferred compounds of formula I are represented by the compounds of formula Ibb

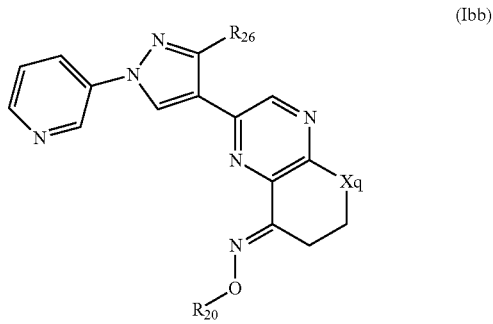

(Ibb)

wherein
$R_{20}$ is hydrogen, $C_1$-$C_6$alkyl or $C_2$-$C_6$alkenyl;
$R_{26}$ is hydrogen or $C_1$-$C_6$alkyl, and
Xq is oxygen, —$CH_2$—, —N($C_1$-$C_6$alkyl)- or —N($C_1$-$C_6$alkylsulfonyl)-.

Further preferred compounds of formula I are represented by the compounds of formula Icc

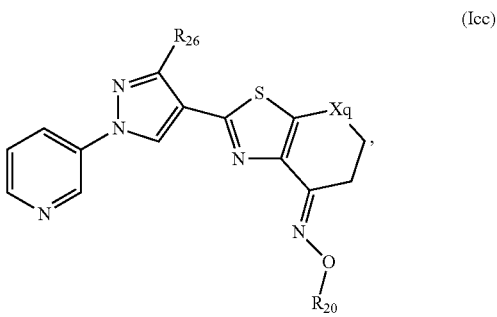

(Icc)

wherein
$R_{20}$ is hydrogen, $C_1$-$C_6$alkyl or $C_2$-$C_6$alkenyl;
$R_{26}$ is hydrogen or $C_1$-$C_6$alkyl, and
Xq is oxygen, —$CH_2$—, —N($C_1$-$C_6$alkyl)- or —N($C_1$-$C_6$alkylsulfonyl)-.

Further preferred compounds of formula I are represented by the compounds of formula Idd (Idd)

wherein
$R_{20}$ is hydrogen, $C_1$-$C_6$alkyl or $C_2$-$C_6$alkenyl;
$R_{26}$ is hydrogen or $C_1$-$C_6$alkyl, and
Xq is oxygen, —$CH_2$—, —N($C_1$-$C_6$alkyl)- or —N($C_1$-$C_6$alkylsulfonyl)-.

Further preferred compounds of formula I are represented by the compounds of formula Iee

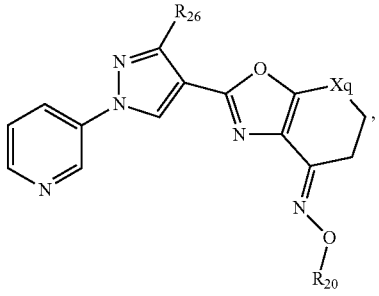
(Iee)

wherein
R$_{20}$ is hydrogen, C$_1$-C$_6$alkyl or C$_2$-C$_6$alkenyl;
R$_{26}$ is hydrogen or C$_1$-C$_6$alkyl, and
Xq is oxygen, —CH$_2$—, —N(C$_1$-C$_6$alkyl)- or —N(C$_1$-C$_6$alkylsulfonyl)-.

Further preferred compounds of formula I are represented by the compounds of formula Iff

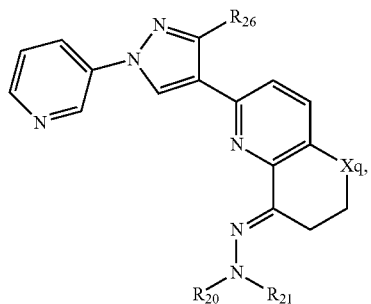
(Iff)

R$_{20}$ is hydrogen or C$_1$-C$_6$alkyl;
R$_{21}$ is hydrogen, C$_1$-C$_6$alkyl, C$_1$-C$_6$alkoxycarbonyl or C$_1$-C$_6$alkylsulfonyl;
R$_{26}$ is hydrogen or C$_1$-C$_6$alkyl, and
Xq is oxygen, —CH$_2$—, —N(C$_1$-C$_6$alkyl)- or —N(C$_1$-C$_6$alkylsulfonyl)-.

Further preferred compounds of formula I are represented by the compounds of formula Igg

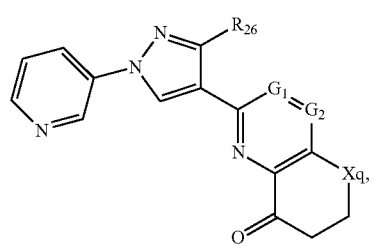
(Igg)

wherein
G$_1$ is CH;
G$_2$ is CH;
R$_{26}$ is hydrogen or C$_1$-C$_6$alkyl, and
Xq is oxygen, —CH$_2$—, —N(C$_1$-C$_6$alkyl)- or —N(C$_1$-C$_6$alkylsulfonyl)-.

Further preferred compounds of formula I are represented by the compounds of formula Ihh

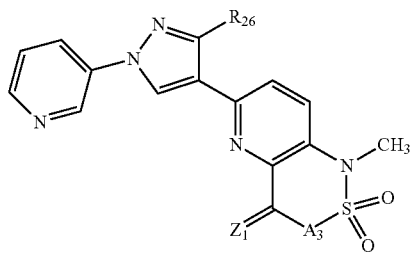
(Ihh)

wherein
R$_{26}$ is hydrogen;
A$_3$ is —CH$_2$— or —C(CH$_3$)$_2$— and
Z$_1$ is O or NO—C$_1$-C$_4$alkyl.

A preferred group of compounds of formula I are represented by the group consisting of the compounds of formulae Iaa, Ibb, Icc, Idd, Iee, Iff, Igg, and Ihh.

Especially preferred compounds of formula I are selected from the compounds of formula I-1

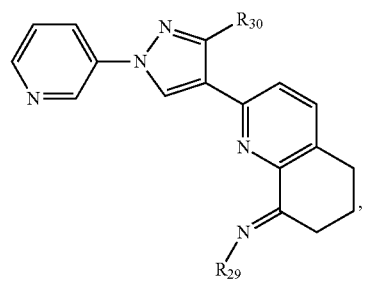
(I-1)

wherein
R$_{29}$ is C$_1$-C$_6$alkoxy, C$_2$-C$_6$alkenyloxy, or N(R$_{31}$)R$_{32}$, wherein
R$_{31}$ is hydrogen or C$_1$-C$_4$alkyl;
R$_{32}$ is C$_1$-C$_6$alkyl or C$_1$-C$_6$alkylcarbonyl; and
R$_{30}$ is hydrogen; the compound of formula I-2

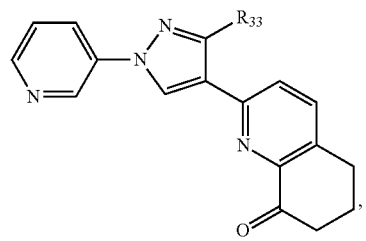
(I-2)

wherein
R$_{33}$ is hydrogen, the compounds of formula Ihh

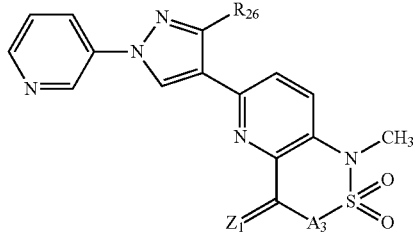

(Ihh)

wherein
R$_{26}$ is hydrogen;
A$_3$ is —CH$_2$— or —C(CH$_3$)$_2$— and
Z$_1$ is O or NO—C$_1$-C$_4$alkyl and the compounds of Table 9 below.

The process according to the invention for preparing compounds of formula I is carried out in principle by methods known to those skilled in the art, or those shown in schemes 1 and 2.

inert solvent, such as DMF, or tetrahydrofurane, with a palladium catalyst, such as Pd(OAc)$_2$, with an appropriate ligand, such as tri-t-butyl phosphine, optionally in the presence of a base such as potassium carbonate, at temperatures between 25-150° C. Such C—H activation technology is known to those skilled in the art, and has been described in, for example, e.g. L. Ackermann et al. *Angew. Chem. Int Ed.*, 48, 9792, 2009, J. Q. Yu, Z. Shi Eds., *Topics in Current Chemistry*, 2010, vol. 292, Springer, or US pat. Appl. 2011212949. Compounds of formula I so obtained can be condensed with either H$_2$NOR$_{20}$, H$_2$NR$_{21}$, H$_2$N—NR$_{22}$R$_{23}$, H$_2$N—N(R$_{24}$)SO$_2$(R$_{25}$), optionally in the presence of a base, for example potassium carbonate, or a dehydrating agent, such as 0.4 nm molecular sieves in an inert solvent, such as tetrahydrofuran, or hexane, or protic solvents, for example ethanol, at temperatures between 25° C. and 150° C., preferably between 25° C. and 80° C. Such chemistries are well known in the literature, for example for compounds where Z$_1$ is N(R$_{24}$)SO$_2$(R$_{25}$) can be prepared according to Ito et al *Bull. Chem. Soc. Japan*, 51, 953, 1978 or Wu et al, *Synthesis*, 249, 1996. For compounds where Z$_1$ is N—OR$_{20}$ a whole range of methods are known for their preparation and to those skilled in the art as exemplified for example in "*Reaktionen der organischen Synthese*", Cesare Ferri, Georg Thieme Verlag, Stuttgart, 1978, p. 540-541.

Scheme 1:

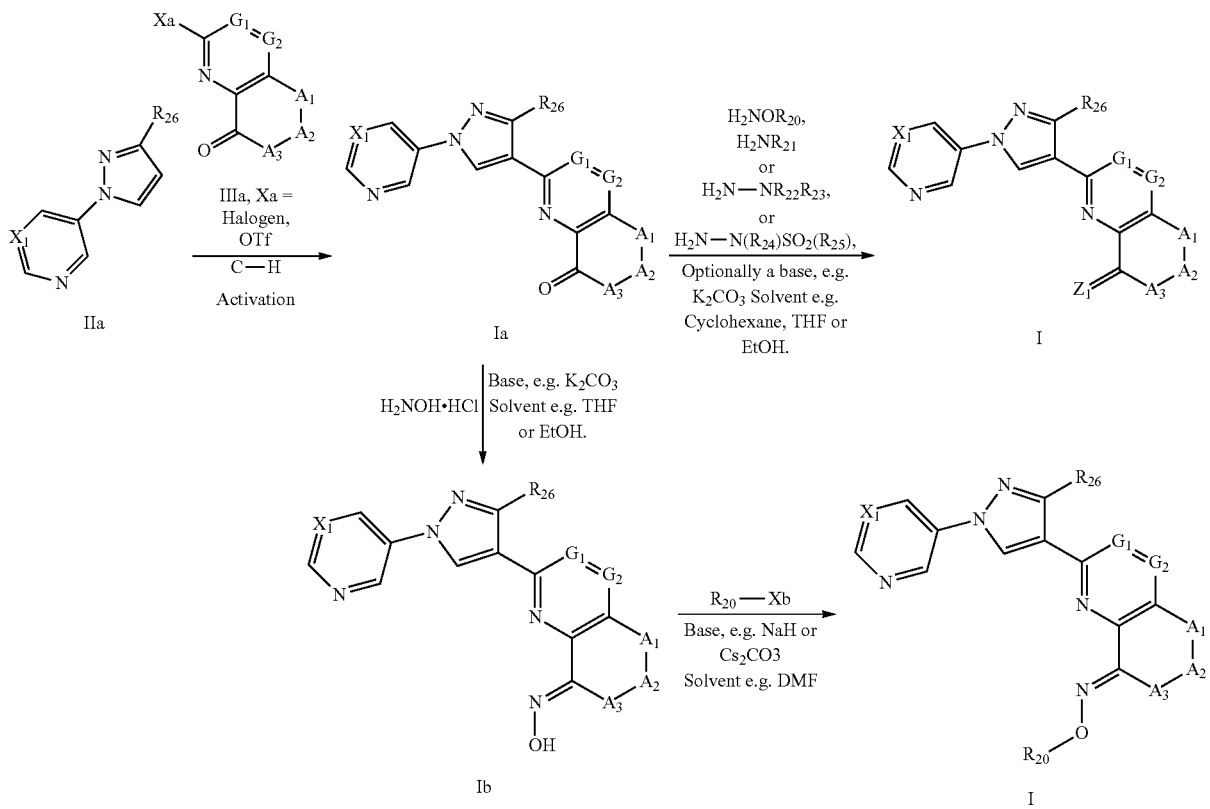

In scheme 1, compounds of formula IIa (prepared as, for example in F. Chevallier et al. *Org. Biomol. Chem.* 2011, 9, 4671) can be coupled to compounds of formula IIIa wherein G$_1$, G$_2$, A$_1$, A$_2$, A$_3$, X$_1$ and R$_{26}$ are defined as described for formula I, and Xa is a leaving group such as halogen or triflate using C—H activation methodology. Here, a compound of formula IIa is treated with a compound of formula IIIa, in an Similarly, compounds of formula I where Z$_1$ is N—NR$_{22}$R$_{23}$, are also readily prepared to those skilled in the art and more specifically as described in "*Reaktionen der organischen Synthese*", Cesare Ferri, Georg Thieme Verlag, Stuttgart, 1978, p. 537-538.

Further synthesis of compounds of formula I are illustrated in scheme 2.

Scheme 2.

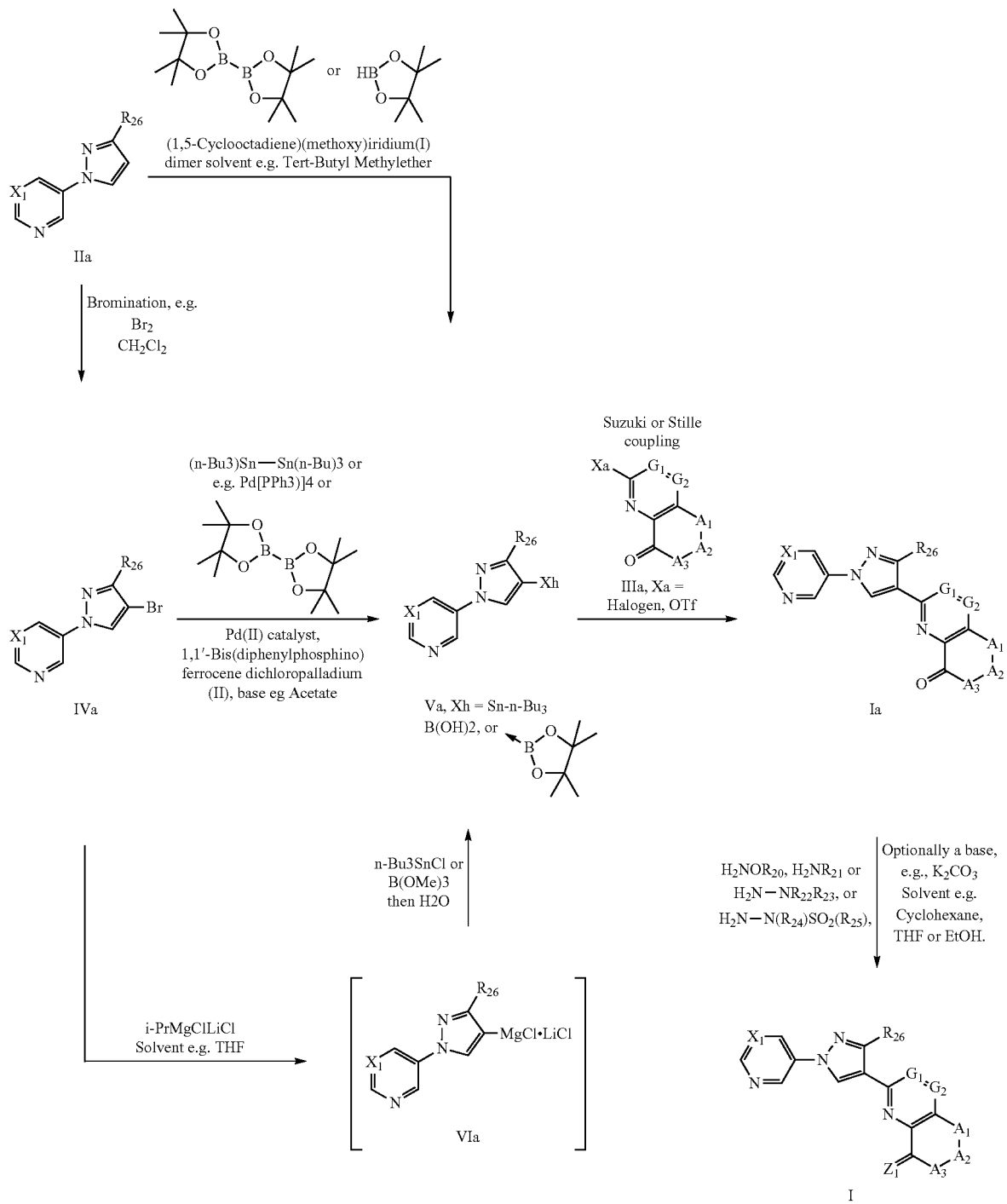

In scheme 2, compounds of formula IIa, prepared as described in for example F. Chevallier et al. *Org. Biomol. Chem.* 2011, 9, 4671, can be converted directly to compounds of formula Va (wherein Xh is pinacolborane) by activating the C—H bond of IIa with an iridium catalyst, e.g. (1,5-Cyclooctadiene)(methoxy)iridium(I) dimer and bis(pinacolato)diboron or pinacolborane in an inert solvent such as tert-butyl methyl ether as described in, for example, *J. Am. Chem. Soc.* 122, 12868, 2000, or *Chem. Rev.,* 110, 890, 2010. Alternatively compound IIa can be converted to the bromide IVa by treatment with bromine in an inert solvent such as dichloromethane. The resultant IVa upon treatment with hexabutyldin, in an inert solvent, such as dioxane, and tetrakis(triphenylphosphine)palladium(0), in the presence of lithium chloride at elevated temperatures leaves to compounds of the formula Va wherein Xh is Sn(n-butyl)$_3$ (see for example *J. Med. Chem,* 48(6), 1886, 2005). In a yet another method to prepare Va wherein Xh is Sn(n-butyl)$_3$, the bromide can be metalated with a Grignard reagent, for example i-PrMgCl·LiCl, in tetrahydrofurane at low temperatures, and the intermediate organo magnesium compound VIa treated with tri-n-butyl tin chloride to give the product IVa, wherein Xh is tri-n-butyl tin.

In a similar fashion, compounds IVa where Xh is a boronic acid, or pinacolborane can be made from the bromine by a using a palladium coupling with bis(pinacolato)diboron as described in for example WO 2012/000896, or by quenching the organo magnesium compound VIa, with trimethoxy borane, followed by aqueous work-up. Compounds of formula Va can then be converted to compounds of formula Ia by Stille or Suzuki coupling as described in scheme 1. The compounds of formula Ia can be converted to compounds of formula I as described in scheme 1.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo [5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound of formula I can be converted in a manner known per se into another compound of formula I by replacing one or more substituents of the starting compound of formula I in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties can be obtained in free form or in the form of salts.

The compounds of formula I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diastereomers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl celulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereose-lective or enantioselective synthesis, for example by carrying out the process according to the invention with starting materials of a suitable stereochemistry.

N-oxides can be prepared by reacting a compound of the formula I with a suitable oxidizing agent, for example the $H_2O_2$/urea adduct in the presence of an acid anhydride, e.g. trifluoroacetic anhydride. Such oxidations are known from the literature, for example from J. Med. Chem., 32 (12), 2561-73, 1989 or WO 00/15615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds of formula I according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i. e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

Examples of the abovementioned animal pests are:
from the order Acarina, for example,

*Acalitus* spp, *Aculus* spp, *Acaricalus* spp, *Aceria* spp, *Acarus siro*, *Amblyomma* spp., *Argas* spp., *Boophilus* spp., *Brevipalpus* spp., *Bryobia* spp, *Calipitrimerus* spp., *Chorioptes* spp., *Dermanyssus gallinae*, *Dermatophagoides* spp., *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.;

from the order Coleoptera, for example,

*Agriotes* spp., *Amphimallon majale*, *Anomala orientalis*, *Anthonomus* spp., *Aphodius* spp, *Astylus atromaculatus*, *Ataenius* spp, *Atomaria linearis*, *Chaetocnema tibialis*, *Cerotoma* spp, *Conoderus* spp, *Cosmopolites* spp., *Cotinis nitida*, *Curculio* spp., *Cyclocephala* spp, *Dermestes* spp., *Diabrotica* spp., *Diloboderus abderus*, *Epilachna* spp., *Eremnus* spp., *Heteronychus arator*, *Hypothenemus hampei*, *Lagria vilosa*, *Leptinotarsa decemLineata*, *Lissorhoptrus* spp., *Liogenys* spp, *Maecolaspis* spp, *Maladera castanea*, *Megascelis* spp, *Melighetes aeneus*, *Melolontha* spp., *Myochrous armatus*, *Orycaephilus* spp., *Otiorhynchus* spp., *Phyllophaga* spp, *Phlyctinus* spp., *Popillia* spp., *Psylliodes* spp., *Rhyssomatus aubtilis*, *Rhizopertha* spp., *Scarabeidae*, *Sitophilus* spp., *Sitotroga* spp., *Somaticus* spp, *Sphenophorus* spp, *Sternechus subsignatus*, *Tenebrio* spp., *Tribolium* spp. and *Trogoderma* spp.;

from the order Diptera, for example,

*Aedes* spp., *Anopheles* spp, *Antherigona soccata*, *Bactrocea oleae*, *Bibio hortulanus*, *Bradysia* spp, *Calliphora erythrocephala*, *Ceratitis* spp., *Chrysomyia* spp., *Culex* spp., *Cuterebra* spp., *Dacus* spp., *Delia* spp, *Drosophila melanogaster*, *Fannia* spp., *Gastrophilus* spp., *Geomyza tripunctata*, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis* spp, *Rivelia quadrifasciata*, *Scatella* spp, *Sciara* spp., *Stomoxys* spp., *Tabanus* spp., *Tannia* spp. and *Tipula* spp.;

from the order Hemiptera, for example,

*Acanthocoris scabrator*, *Acrosternum* spp, *Adelphocoris lineolatus*, *Amblypelta nitida*, *Bathycoelia thalassina*, *Blissus* spp, *Cimex* spp., *Clavigralla tomentosicollis*, *Creontiades* spp, *Distantiella theobroma*, *Dichelops furcatus*, *Dysdercus* spp., *Edessa* spp, *Euchistus* spp., *Eurydema pulchrum*, *Eurygaster* spp., *Halyomorpha halys*, *Horcias nobilellus*, *Leptocorisa* spp., *Lygus* spp, *Margarodes* spp, *Murgantia histrionic*, *Neomegalotomus* spp, *Nesidiocoris tenuis*, *Nezara* spp., *Nysius simulans*, *Oebalus insularis*, *Piesma* spp., *Piezodorus* spp, *Rhodnius* spp., *Sahlbergella singularis*, *Scaptocoris castanea*, *Scotinophara* spp., *Thyanta* spp, *Triatoma* spp., *Vatiga illudens*;

*Acyrthosium pisum*, *Adalges* spp, *Agalliana ensigera*, *Agonoscena targionii*, *Aleurodicus* spp, *Aleurocanthus* spp, *Aleurolobus barodensis*, *Aleurothrixus floccosus*, *Aleyrodes brassicae*, *Amarasca biguttula*, *Amritodus atkinsoni*, *Aonidiella* spp., *Aphididae*, *Aphis* spp., *Aspidiotus* spp., *Aulacorthum solani*, *Bactericera cockerelli*, *Bemisia* spp, *Brachycaudus* spp, *Brevicoryne brassicae*, *Cacopsylla* spp, *Cavariella aegopodii* Scop., *Ceroplaster* spp., *Chrysomphalus aonidium*, *Chrysomphalus dictyospermi*, *Cicadella* spp, *Cofana spectra*, *Cryptomyzus* spp, *Cicadulina* spp, *Coccus hesperidum*, *Dalbulus maidis*, *Dialeurodes* spp, *Diaphorina citri*, *Diuraphis noxia*, *Dysaphis* spp, *Empoasca* spp., *Eriosoma larigerum*, *Erythroneura* spp., *Gascardia* spp., *Glycaspis brimblecombei*, *Hyadaphis pseudobrassicae*, *Hyalopterus* spp, *Hyperomyzus pallidus*, *Idioscopus clypealis*, *Jacobiasca lybica*, *Laodelphax* spp., *Lecanium corni*, *Lepidosaphes* spp., *Lopaphis erysimi*, *Lyogenys maidis*, *Macrosiphum* spp., *Mahanarva* spp, *Metcalfa pruinosa*, *Metopolophium dirhodum*, *Myndus crudus*, *Myzus* spp., *Neotoxoptera* sp, *Nephotettix* spp., *Nilaparvata* spp., *Nippolachnus piri* Mats, *Odonaspis ruthae*, *Oregma lanigera* Zehnter, *Parabemisia myricae*, *Paratrioza cockerelli*, *Parlatoria* spp., *Pemphigus* spp., *Peregrinus maidis*, *Perkinsiella* spp, *Phorodon humuli*, *Phylloxera* spp, *Planococcus* spp., *Pseudaulacaspis* spp., *Pseudococcus* spp., *Pseudatomoscelis seriatus*, *Psylla* spp., *Pulvinaria aethiopica*, *Quadraspidiotus* spp., *Quesada gigas*, *Recilia dorsalis*, *Rhopalosiphum* spp., *Saissetia* spp., *Scaphoideus* spp., *Schizaphis* spp., *Sitobion* spp., *Sogatella furcifera*, *Spissistilus festinus*, *Tarophagus Proserpina*, *Toxoptera* spp, *Trialeurodes* spp, *Tridiscus sporoboli*, *Trionymus* spp, *Trioza erytreae*, *Unaspis citri*, *Zygina flammigera*, *Zyginidia scutellaris*;

from the order Hymenoptera, for example,

*Acromyrmex*, *Arge* spp, *Atta* spp., *Cephus* spp., *Diprion* spp., *Diprionidae*, *Gilpinia polytoma*, *Hoplocampa* spp., *Lasius* spp., *Monomorium pharaonis*, *Neodiprion* spp., *Pogonomyrmex* spp, *Slenopsis invicta*, *Solenopsis* spp. and *Vespa* spp.;

from the order Isoptera, for example,

*Coptotermes* spp, *Corniternes cumulans*, *Incisitermes* spp, *Macrotermes* spp, *Mastotermes* spp, *Microtermes* spp, *Reticulitermes* spp.; *Solenopsis* geminate from the order Lepidoptera, for example,

*Acleris* spp., *Adoxophyes* spp., *Aegeria* spp., *Agrotis* spp., *Alabama argillaceae*, *Amylois* spp., *Anticarsia gemmatalis*, *Archips* spp., *Argyresthia* spp, *Argyrotaenia* spp., *Autographa* spp., *Bucculatrix thurberiella*, *Busseola fusca*, *Cadra cautella*, *Carposina nipponensis*, *Chilo* spp., *Choristoneura* spp., *Chrysoteuchia topiaria*, *Clysia ambiguella*, *Cnaphalocrocis* spp., *Cnephasia* spp., *Cochylis* spp., *Coleophora* spp., *Colias lesbia*, *Cosmophila flava*, *Crambus* spp, *Crocidolomia binotalis*, *Cryptophlebia leucotreta*, *Cydalima perspectalis*, *Cydia* spp., *Diaphania perspectalis*, *Diatraea* spp., *Diparopsis castanea*, *Earias* spp., *Eldana saccharina*, *Ephestia* spp., *Epinotia* spp, *Estigmene acrea*, *Etiella zinckinella*, *Eucosma* spp., *Eupoecilia ambiguella*, *Euproctis* spp., *Euxoa* spp., *Feltia jaculiferia*, *Grapholita* spp., *Hedya nubiferana*, *Heliothis* spp., *Hellula undalis*, *Herpetogramma* spp, *Hyphantria cunea*, *Keiferia lycopersicella*, *Lasmopalpus lignosellus*, *Leucoptera scitella*, *Lithocollethis* spp., *Lobesia botrana*, *Loxostege bifidalis*, *Lymantria* spp., *Lyonetia* spp., *Malacosoma* spp., *Mamestra brassicae*, *Manduca sexta*, *Mythimna* spp, *Noctua* spp, *Operophtera* spp., *Orniodes indica*, *Ostrinia nubilalis*, *Pammene* spp., *Pandemis* spp., *Panolis flammea*, *Papaipema nebris*, *Pectinophora gossypiela*, *Perileucoptera coffeella*, *Pseudaletia unipuncta*, *Phthorimaea operculella*, *Pieris rapae*, *Pieris* spp., *Plutella xylostella*, *Prays* spp., *Pseudoplusia* spp, *R achiplusia nu*, *Richia albicosta*, *Scirpophaga* spp., *Sesamia* spp., *Sparganothis* spp., *Spodoptera* spp., *Sylepta derogate*, *Synanthedon* spp., *Thaumetopoea* spp., *Tortrix* spp., *Trichoplusia ni*, *Tuta absoluta*, and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae*, *Locusta* spp., *Neocurtilla hexadactyla*, *Periplaneta* spp., *Scapteriscus* spp, and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis;* from the order Thysanoptera, for example,

*Calliothrips phaseoli*, *Frankliniella* spp., *Heliothrips* spp, *Hercinothrips* spp., *Parthenothrips* spp, *Scirtothrips aurantii*, *Sericothrips variabilis*, *Taeniothrips* spp., *Thrips* spp;

from the order Thysanura, for example, *Lepisma saccharina*.

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals.

The active ingredients according to the invention are especially suitable for controlling *Aphis craccivora*, *Diabrotica balteata*, *Heliothis virescens*, *Myzus persicae*, *Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca*(preferably in vegetables, vineyards), *Leptinotarsa* (preferably in potatoes) and *Chilo supressalis* (preferably in rice).

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla*, *Meloidogyne incognita*, *Meloidogyne javanica*, *Meloidogyne arenaria* and other *Meloidogyne* species; cyst-forming nematodes, *Globodera rostochiensis* and other *Globodera* species; *Heterodera avenae*, *Heterodera glycines*, *Heterodera schachtii*, *Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus* destructor, *Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus*, *Pratylenchus penetrans*, *Pratylenchus curvitatus*, *Pratylenchus goodeyi* and other *Pratylenchus* species; Burrowing nematodes, *Radopholus similis* and other *Radopholus* species; Reniform nematodes, *Rotylenchus robustus*, *Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni*, *Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

The compounds of the invention may also have activity against the molluscs. Examples of which include, for example, *Ampullariidae;* *Anion* (*A. ater*, *A. circumscriptus*, *A. hortensis*, *A. rufus*); Bradybaenidae (*Bradybaena fruticum*); *Cepaea* (*C. hortensis*, *C. Nemoralis*); *ochlodina*; *Deroceras* (*D. agrestis*, *D. empiricorum*, *D. laeve*, *D. reticulatum*); *Discus* (*D. rotundatus*); *Euomphalia*; *Galba* (*G. trunculata*);

*Helicelia* (*H. itala, H. obvia*); Helicidae *Helicigona arbustorum*); *Helicodiscus; Helix* (*H. aperta*); *Limax* (*L. cinereoniger, L. flavus, L. marginatus, L. maximus, L. tenellus*); *Lymnaea; Milax* (*M. gagates, M. marginatus, M. sowerbyi*); *Opeas; Pomacea* (*P. canaticulata*); *Vallonia* and *Zanitoides*.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cry1-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and moths (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); Nature-Gard®, Agrisure® GT Advantage (GA21 glyphosate-tolerant trait), Agrisure® CB Advantage (Bt11 corn borer (CB) trait) and Protecta®.

Further examples of such transgenic crops are:
1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.
3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.
4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.
7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from

*Bacillus thuringiensis* subsp. *kurstaki* which brings about tolerance to certain Lepidoptera, include the European corn borer.

Transgenic crops of insect-resistant plants are also described in BATS (Zentrum für Biosicherheit and Nachhaltigkeit, Zentrum BATS, Clarastrasse 13, 4058 Basel, Switzerland) Report 2003, (http://bats.ch).

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defense (so-called "plant disease resistance genes", as described in WO 03/000906).

Further areas of use of the compositions according to the invention are the protection of stored goods and store rooms and the protection of raw materials, such as wood, textiles, floor coverings or buildings, and also in the hygiene sector, especially the protection of humans, domestic animals and productive livestock against pests of the mentioned type. In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis, Periplaneta americana, Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergatesspp., Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capucins, Heterobostrychus brunneus, Sinoxylon* spec. and *Dinoderus minutus*, and also hymenopterans such as *Sirex juvencus, Urocerus gigas, Urocerus gigas taignus* and *Urocerus augur*, and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharina.*

The invention therefore also relates to pesticidal compositions such as emulsifiable concentrates, suspension concentrates, microemulsions, oil dispersibles, directly sprayable or dilutable solutions, spreadable pastes, dilute emulsions, soluble powders, dispersible powders, wettable powders, dusts, granules or encapsulations in polymeric substances, which comprise—at least—one of the active ingredients according to the invention and which are to be selected to suit the intended aims and the prevailing circumstances. In these compositions, the active ingredient is employed in pure form, a solid active ingredient for example in a specific particle size, or, preferably, together with—at least—one of the auxiliaries conventionally used in the art of formulation, such as extenders, for example solvents or solid carriers, or such as surface-active compounds (surfactants).

Examples of suitable solvents are: unhydrogenated or partially hydrogenated aromatic hydrocarbons, preferably the fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, isophorone or diacetone alcohol, strongly polar solvents, such as N-me-thylpyrrolid-2-one, dimethyl sulfoxide or N,N-dimethylformamide, water, unepoxidized or epoxidized vegetable oils, such as unexpodized or epoxidized rapeseed, castor, coconut or soya oil, and silicone oils.

Solid carriers which are used for example for dusts and dispersible powders are, as a rule, ground natural minerals such as calcite, talc, kaolin, montmorillonite or attapulgite. To improve the physical properties, it is also possible to add highly disperse silicas or highly disperse absorbtive polymers. Suitable adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature.

Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopo-lypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propylene glycol unit. Examples which may be mentioned are nonylphenoxypolyethoxyethanol, castor oil polyglycol ether, polypropylene glycol/polyethylene oxide adducts, tributylpheno-xypolyethoxyethanol, polyethylene glycol or octylphenoxypolyethoxyethanol. Also suitable are fatty acid esters of polyoxyethylene sorbitan, such as polyoxyethylene sorbitan trioleate. The cationic surfactants are, especially, quarternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates. Examples are stearyltrimethylammonium chloride and benzylbis(2-chloroethyl)ethyl-ammonium bromide.

Examples of suitable anionic surfactants are water-soluble soaps or water-soluble synthetic surface-active compounds. Examples of suitable soaps are the alkali, alkaline earth or (unsubstituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2 sulfonyl groups and a fatty acid radical of approximately 8 to approximately 22 C atoms. Examples of alkylarylsulfonates are the sodium, calcium or triethanolammonium salts of decylbenzenesulfonic acid, of dibutyl-naphthalenesulfonic acid or of a naphthalenesulfonic acid/formaldehyde condensate. Also possible are, furthermore, suitable phosphates, such as salts of the phosphoric ester of a p-nonylphenol/(4-14)ethylene oxide adduct, or phospholipids.

As a rule, the compositions comprise 0.1 to 99%, especially 0.1 to 95%, of active ingredient and 1 to 99.9%, especially 5 to 99.9%, of at least one solid or liquid adjuvant, it being possible as a rule for 0 to 25%, especially 0.1 to 20%, of the composition to be surfactants(% in each case meaning percent by weight). Whereas concentrated compositions tend to be preferred for commercial goods, the end consumer as a rule uses dilute compositions which have substantially lower concentrations of active ingredient.

Typically, a pre-mix formulation for foliar application comprises 0.1 to 99.9%, especially 1 to 95%, of the desired ingredients, and 99.9 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Normally, a tank-mix formulation for seed treatment application comprises 0.25 to 80%, especially 1 to 75%, of the desired ingredients, and 99.75 to 20%, especially 99 to 25%, of a solid or liquid auxiliaries (including, for example, a solvent such as water), where the auxiliaries can be a surfactant in an amount of 0 to 40%, especially 0.5 to 30%, based on the tank-mix formulation.

Typically, a pre-mix formulation for seed treatment application comprises 0.5 to 99.9%, especially 1 to 95%, of the desired ingredients, and 99.5 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Whereas commercial products will preferably be formulated as concentrates (e.g., pre-mix composition (formulation)), the end user will normally employ dilute formulations (e.g., tank mix composition).

Preferred seed treatment pre-mix formulations are aqueous suspension concentrates. The formulation can be applied to the seeds using conventional treating techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art. In general, the pre-mix compositions of the invention contain 0.5 to 99.9 especially 1 to 95, advantageously 1 to 50%, by mass of the desired ingredients, and 99.5 to 0.1, especially 99 to 5%, by mass of a solid or liquid adjuvant (including, for example, a solvent such as water), where the auxiliaries (or adjuvant) can be a surfactant in an amount of 0 to 50, especially 0.5 to 40%, by mass based on the mass of the pre-mix formulation.

Examples of foliar formulation types for pre-mix compositions are:
GR: Granules
WP: wettable powders
WG: water dispersable granules (powders)
SG: water soluble granules SL: soluble concentrates
EC: emulsifiable concentrate
EW: emulsions, oil in water
ME: micro-emulsion
SC: aqueous suspension concentrate
CS: aqueous capsule suspension
OD: oil-based suspension concentrate, and
SE: aqueous suspo-emulsion.

Whereas, examples of seed treatment formulation types for pre-mix compositions are:
WS: wettable powders for seed treatment slurry
LS: solution for seed treatment
ES: emulsions for seed treatment
FS: suspension concentrate for seed treatment
WG: water dispersible granules, and
CS: aqueous capsule suspension.

Examples of formulation types suitable for tank-mix compositions are solutions, dilute emulsions, suspensions, or a mixture thereof, and dusts.

Preferred compositions are composed in particular as follows (%=percent by weight):
Emulsifiable Concentrates:
active ingredient: 1 to 95%, preferably 5 to 20%
surfactant: 1 to 30%, preferably 10 to 20%
solvent: 5 to 98%, preferably 70 to 85%
Dusts:
active ingredient: 0.1 to 10%, preferably 0.1 to 1%
solid carrier: 99.9 to 90%, preferably 99.9 to 99%
Suspension Concentrates:
active ingredient: 5 to 75%, preferably 10 to 50%
water: 94 to 24%, preferably 88 to 30%
surfactant: 1 to 40%, preferably 2 to 30%
Wettable Powders:
active ingredient: 0.5 to 90%, preferably 1 to 80%
surfactant: 0.5 to 20%, preferably 1 to 15%
solid carrier: 5 to 99%, preferably 15 to 98%
Granulates:
active ingredient: 0.5 to 30%, preferably 3 to 15%
solid carrier: 99.5 to 70%, preferably 97 to 85%

PREPARATORY EXAMPLES

"mp" means melting point in ° C.

Example P1

Preparation of 2-(1-pyridin-3-yl-1H-pyrazol-4-yl)-6,7-dihydro-5H-quinolin-8-one (Compound 7.002)

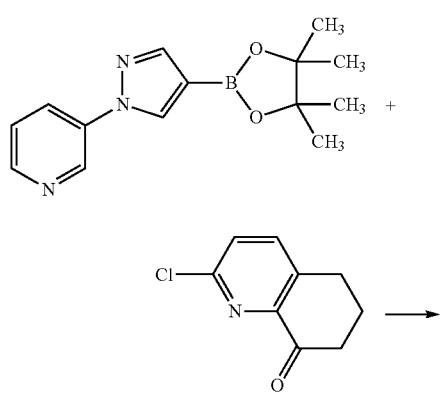

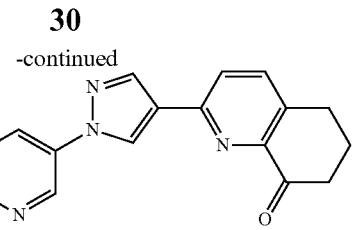

A mixture of 2-chloro-6,7-dihydro-8(5H)-quinolinone (1.14 g, 6.3 mmol, prepared as described in *J. Org. Chem.* 1990, 55, 4789) and 3-[4-(4,4,5,5-tetramethyl-[1,3,2]dioxaborolan-2-yl)-pyrazol-1-yl]-pyridine (1.7 g, 6.3 mmol, WO 2012/000896), sodium carbonate (3.15 g, 29.6 mmol) in a mixture of acetonitrile (50 ml) and water (30 ml) was purged with argon for 10 min. To this solution was added Pd[P(Ph)$_3$]$_4$ (270 mg, 0.23 mmol) and the solution was heated at 80° C. overnight. The reaction mixture was diluted with ethyl acetate and the water phase was separated. The organic phase was washed with brine and dried over anhydrous MgSO$_4$, filtered and concentrated in vacuo. The residue was crystallized in isopropanol/petrol ether (1:1) to give two crops of the title product as a beige solid.

LCMS: 0.72 min, 291 (M+1), mp: 158-9° C.

Example P2

Preparation of 2-(1-pyridin-3-yl-1H-pyrazol-4-yl)-6,7-dihydro-5H-quinolin-8-one O-isopropyl-oxime (Compound 1.005)

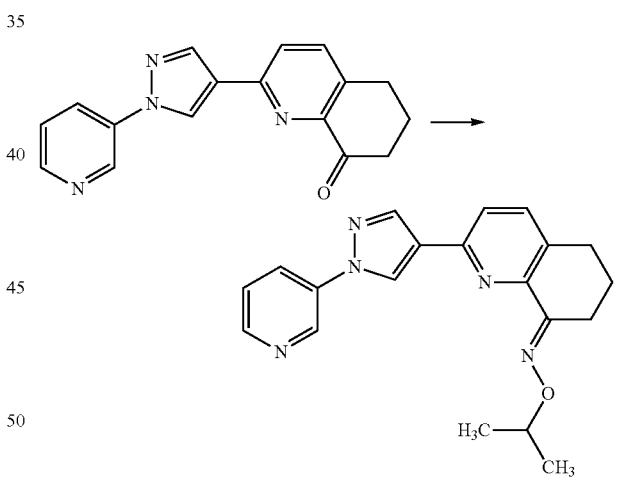

A solution of 2-(1-pyridin-3-yl-1H-pyrazol-4-yl)-6,7-dihydro-5H-quinolin-8-one (125 mg, 0.43 mmol) was dissolved in ethanol (5 ml) and sodium acetate (54 mg, 0.65 mmol) was added at ambient temperature. To this was added 0-isopropyl-hydroxylamine hydrochloride (62.4 mg, 0.56 mmol) and the resulting yellowish suspension was heated at reflux overnight. The reaction mixture was evaporated to dryness and taken up in ethyl acetate. The organic phase was washed with brine, dried over anhydrous MgSO$_4$, filtered and concentrated in vacuo. The residue was crystallised in disopropylether to give the title compound as a beige solid, and as a single isomer.

LCMS: 1.0 min, 348 (M+1), mp: 128-130° C.

Example P3

Preparation of acetic acid [2-(1-pyridin-3-yl-1H-pyrazol-4-yl)-6,7-dihydro-5H-quinolin-ylidene]-hydrazide (Compound 6.007)

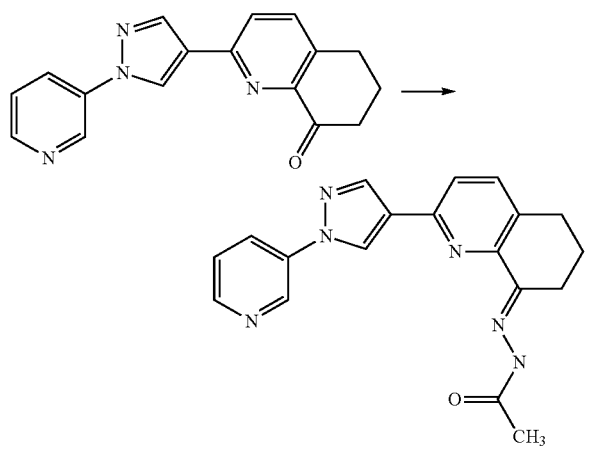

A solution of 2-(1-pyridin-3-yl-1H-pyrazol-4-yl)-6,7-dihydro-5H-quinolin-8-one (125 mg, 0.43 mmol) and acetic acid hydrazide (47 mg, 0.63 mmol) in ethanol (5 ml) was heated at 75° C. overnight. The reaction mixture was evaporated to dryness, the residue was taken up in ethyl acetate and washed twice with water. The organic phase was dried over anhydrous MgSO$_4$, filtered and concentrated in vacuo. Purification by flash chromatography eluting with ethyl acetate/methanol 19:1 gave the title product as white solid.

LCMS: 0.89 min, 347 (M+1)

Example P4

Preparation of N-ethoxy-2-hydroxy-1-methyl-2-oxo-6-[1-(3-pyridyl)pyrazol-4-yl]pyrido[3,2-c]thiazin-4-imine (Compound 8.003)

Example P4.1

Preparation of ethyl 6-bromo-3-(methanesulfonamido)pyridine-2-carboxylate

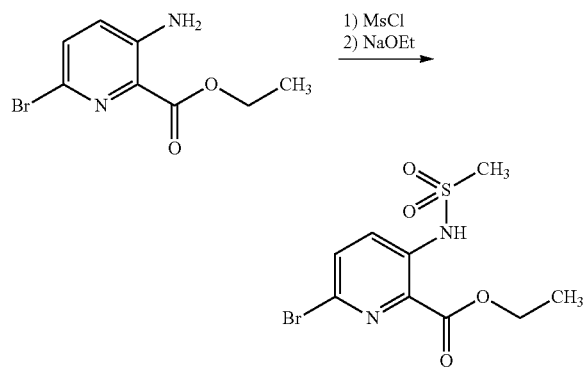

Step 1: To a solution of ethyl 3-amino-6-bromo-pyridine-2-carboxylate (3.33 g, 13.6 mmol, prepared from commercial 3-amino anthranilic acid according to WO 2010/141406) in THF (100 ml) was added triethylamine (40 ml, 288 mmol) at 0° C. followed by MsCl (10 ml, 129 mmol). The thick suspension was stirred at 55° C. for 14.5 hours. The mixture was allowed to cool to ambient temperature then LCMS showed complete conversion to the mono and bismesylated product in roughly 1/1 ratio. The crude mixture was quenched by addition of water and ethyl acetate. Separation of phases, extraction with ethyl acetate (twice) then drying over Na$_2$SO$_4$ and evaporation afforded the crude material which was taken to the next step.

Step 2: To the aforementioned mixture of mono and bismesylated products was added ethanol (100 ml) followed by sodium ethanolate (21%, 5.6 ml, 15 mmol) at ambient temperature leading to an almost complete solution. Stirring was continued for 1 hour then the solution was concentrated under reduced pressure followed by addition of water, NH$_4$Cl (sat. aq.) and ethyl acetate. The phases were separated followed by extraction of the aqueous phase with ethyl acetate, drying over Na$_2$SO$_4$ and evaporation affording 6-bromo-3-(methanesulfonamido)pyridine-2-carboxylate as a yellow solid.

LCMS: 0.84 min, 323, 325 (M+1) (Br isotope pattern).

Example P4.2

Preparation of ethyl 6-bromo-3-[methyl(methylsulfonyl)amino]pyridine-2-carboxylate

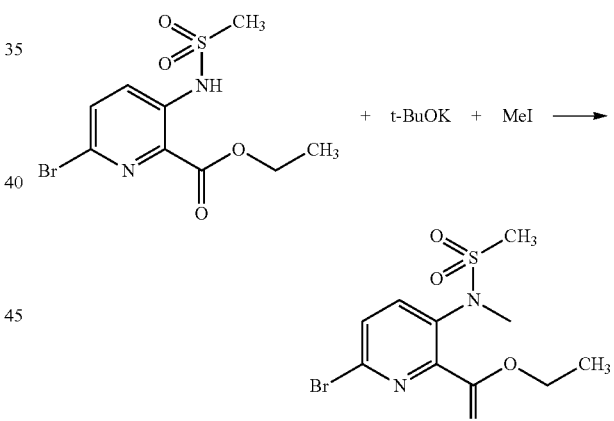

To a solution of ethyl 6-bromo-3-(methanesulfonamido)pyridine-2-carboxylate (8.12 g, 25.1 mmol) in dry DMSO (60 ml) was added KOtBu (3.1 g, 27.6 mmol) while applying a water bath and stirring was continued for 1 hour. The water bath was removed followed by addition of MeI (3.13 ml, 50.3 mmol) at rt and stirring was continued for 1 hour. The solution was poured onto ice (100 mL), ethyl acetate was added then the phases were separated followed by extraction of the aqueous phase with ethyl acetate (twice). The combined organic phases were dried over Na$_2$SO$_4$, filtered and concentrated in vacuo. Purification by flash chromatography eluting with ethyl acetate/heptane, gradient, afforded 6-bromo-3-[methyl(methylsulfonyl)amino]pyridine-2-carboxylate as a yellow semi-solid.

LCMS: 0.78 min, 337, 339 (M+1) (Br isotope pattern).

Example P4.3

Preparation of 6-bromo-1-methyl-2,2-dioxo-pyrido[3,2-c]thiazin-4-one

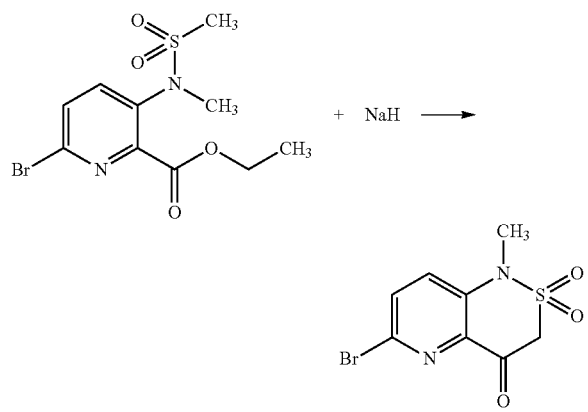

To a three necked flask flushed with argon was added NaH (60%, 0.75 g, 18.7 mmol) followed by DMF (10 ml) and stirring was continued for 5 min followed by addition of a solution of ethyl 6-bromo-3-[methyl(methylsulfonyl)amino]pyridine-2-carboxylate (3.16 g, 9.37 mmol) in DMF (35 ml, rinsed with 2×2.5 ml) at ambient temperature giving a reddish solution under effervescence. After stirring for 1 hour the reaction mixture was concentrated under reduced pressure followed by addition of water and ethyl acetate then the phases were separated. The acqueous phase was made slightly acidic using $H_2SO_4$ (95-97%) followed by extraction with methylene chloride. The combined organic phases were dried over $Na_2SO_4$, filtered and concentrated in vacuo. Purification by flash chromatography eluting with ethyl acetate/heptane, gradient, afforded 6-bromo-1-methyl-2,2-dioxo-pyrido[3,2-c]thiazin-4-one as a yellow solid.

LCMS: 0.60 min, 219, 293 (M+1) (Br isotope pattern).

Example P4.4

Preparation of 6-bromo-N-ethoxy-1-methyl-2,2-dioxo-pyrido[3,2-c]thiazin-4-imine

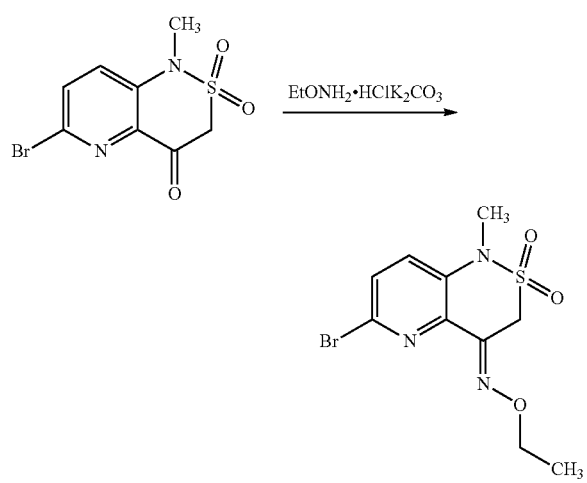

To a suspension of $EtONH_2 \cdot HCl$ (171 mg, 2.06 mmol) in EtOH (5 ml) was added $K_2CO_3$ (288 mg, 2.06 mmol) and stirring was continued for 20 min at ambient temperature. A solution of 6-bromo-1-methyl-2,2-dioxo-pyrido[3,2-c]thiazin-4-one (500 mg, 1.72 mmol) in EtOH (5 ml) was added and stirring was continued for 12 h affording a milky suspension. Since the conversion was not complete, the same amount of $EtONH_2 \cdot HCl$ in EtOH and $K_2CO_3$ were separately mixed and added to the reaction mixture affording after 60 min full conversion. The mixture was concentrated under reduced pressure followed by addition of water and ethyl acetate then the phases were separated. The aqueous phase was extracted with ethyl acetate. The combined organic phases were dried over $Na_2SO_4$, filtered and concentrated in vacuo. Purification by flash chromatography eluting with ethyl acetate/heptane, gradient, afforded 6-bromo-N-ethoxy-1-methyl-2,2-dioxo-pyrido[3,2-c]thiazin-4-imine as a yellow solid and a single isomer.

LCMS: 0.84 min, 334, 336 (M+1) (Br isotope pattern).

Example P4.5

Preparation of N-ethoxy-2-hydroxy-1-methyl-2-oxo-6-[1-(3-pyridyl)pyrazol-4-yl]pyrido[3,2-c]thiazin-4-imine (Compound 8.003)

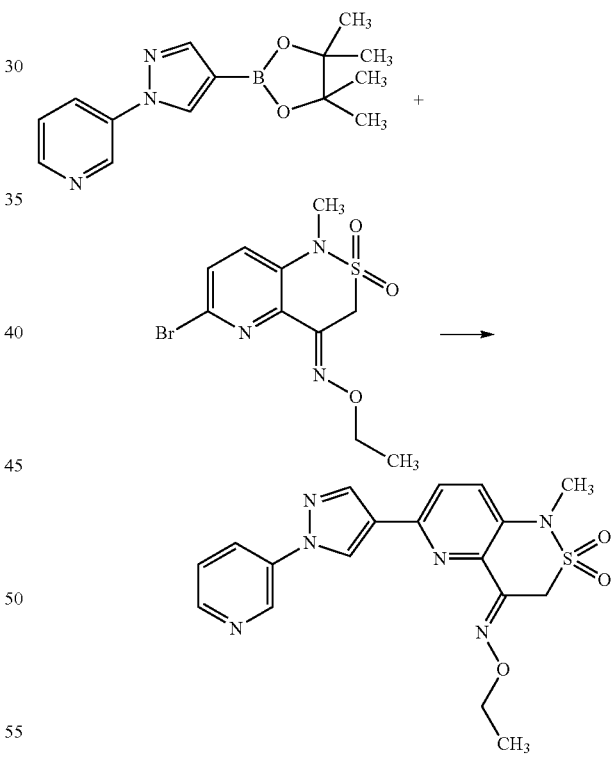

To $Na_2CO_3$ (183 mg, 1.71 mmol) was added water (1.5 ml) and acetonitrile (2 ml) and the solution was degassed for 5 min with argon. 3-[4-(4,4,5,5-tetramethyl-1,3,2-dioxaborolan-2-yl)pyrazol-1-yl]pyridine (111 mg, 0.41 mmol), 6-bromo-N-ethoxy-1-methyl-2,2-dioxo-pyrido[3,2-c]thiazin-4-imine (114 mg, 0.34 mmol) and Pd(dppf)Cl$_2$ (25 mg, 0.034 mmol) were added sequentially followed by rinsing the flask with acetonitrile (2 ml). The mixture was stirred at 80° C. for 1.5 h followed by cooling to ambient temperature. Water and ethyl acetate were added then the phases were separated. The aqueous phase was extracted with ethyl acetate. The combined organic phases were dried over Na₂SO₄, filtered and concentrated in vacuo. Purification by flash chromatography eluting with ethyl acetate/heptane, gradient, afforded N-ethoxy-1-methyl-2,2-dioxo-6-[1-(3-pyridyl)pyrazol-4-yl]pyrido[3,2-c]thiazin-4-imine as a red solid as a single isomer.

LCMS: 0.83 min, 399 (M+1).

Example P5

Preparation of N-methoxy-1,3,3-trimethyl-2,2-dioxo-6-[1-(3-pyridyl)pyrazol-4-yl]pyrido[3,2-c]thiazin-4-imine (Compounds 8.004 and 8.005)

Example P5.1

Preparation of 6-bromo-1,3,3-trimethyl-2,2-dioxo-pyrido[3,2-c]thiazin-4-one

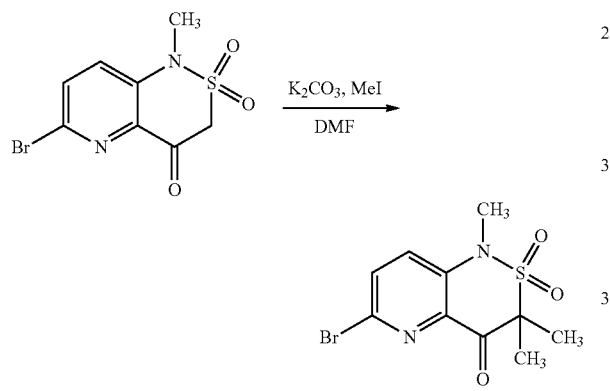

To a solution of 6-bromo-1-methyl-2,2-dioxo-pyrido[3,2-c]thiazin-4-one (456 mg, 1.56 mmol) in DMF (3 ml) was added K₂CO₃ (2.16 g, 15.6 mmol) followed by MeI (0.29 ml, 4.7 mmol) at ambient temperature. The suspension was heated to 60° C. for 1.5 h then cooled to ambient temperature, filtered, washed with ethyl acetate and concentrated under reduced pressure. Purification by flash chromatography eluting with ethyl acetate/heptane, gradient, afforded 6-bromo-1,3,3-trimethyl-2,2-dioxo-pyrido[3,2-c]thiazin-4-one.

LCMS: 0.78 min, 319, 321 (M+1) (Br isotope pattern).

Example P5.2

Preparation 6-bromo-N-methoxy-1,3,3-trimethyl-2,2-dioxo-pyrido[3,2-c]thiazin-4-imine

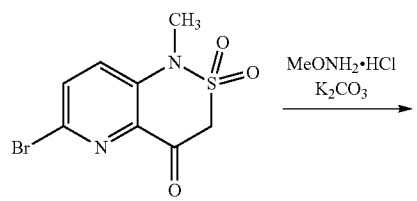

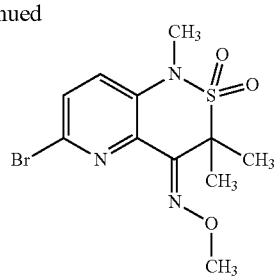

To a suspension of MeONH₂.HCl (272 mg, 3.26 mmol) in pyridine (5 ml) was added 6-bromo-1,3,3-trimethyl-2,2-dioxo-pyrido[3,2-c]thiazin-4-one (130 mg, 0.41 mmol) and stirring was continued for 2 days at 100° C. The mixture was cooled to ambient temperature then concentrated under reduced pressure followed by addition of water and ethyl acetate then the phases were separated. The aqueous phase was extracted with ethyl acetate. The combined organic phases were dried over Na₂SO₄, filtered and concentrated in vacuo. Purification by flash chromatography eluting with ethyl acetate/heptane, gradient, afforded 6-bromo-N-methoxy-1,3,3-trimethyl-2,2-dioxo-pyrido[3,2-c]thiazin-4-imine as a yellow solid as a 5/1 mixture of oxime isomers.

LCMS: 0.89 min, 348, 350 (M+1) (Br isotope pattern).

Example P5.3

Preparation of N-methoxy-1,3,3-trimethyl-2,2-dioxo-6-[1-(3-pyridyl)pyrazol-4 yl]pyrido[3,2-c]thiazin-4-imine

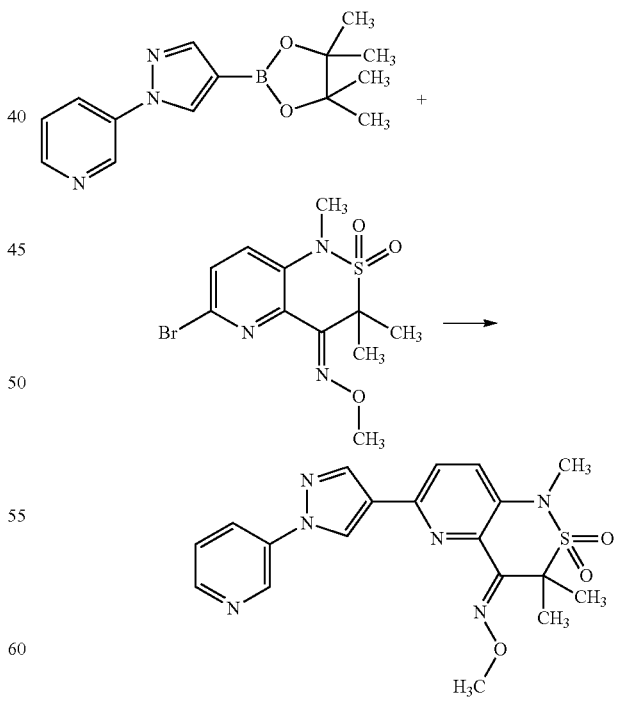

To Na₂CO₃ (180 mg, 1.68 mmol) was added water (1.5 ml) and acetonitrile (2 ml) and the solution was degassed for 5 min with argon. 3-[4-(4,4,5,5-tetramethyl-1,3,2-dioxaborolan-2-yl)pyrazol-1-yl]pyridine (109 mg, 0.40 mmol), a solution of 6-bromo-N-methoxy-1,3,3-trimethyl-2,2-dioxo-pyrido[3,2-c]thiazin-4-imine (117 mg, 0.34 mmol) in acetonitrile (2 ml) and Pd(dppf)Cl$_2$ (13 mg, 0.017 mmol) were added sequentially followed by rinsing the flask with acetonitrile (1 ml). The mixture was stirred at 100° C. for 1 h then allowed to cool to ambient temperature. Water and ethyl acetate were added then the phases were separated. The aqueous phase was extracted with ethyl acetate. The combined organic phases were dried over Na$_2$SO$_4$, filtered and concentrated in vacuo. Purification by chromatography afforded two oxime isomers of N-methoxy-1,3,3-trimethyl-2,2-dioxo-6-[1-(3-pyridyl)pyrazol-4 yl]pyrido[3,2-c]thiazin-4-imine.

Isomer 1: LCMS: 0.86 min, 413 (M+1), mp: 197-199° C.
Isomer 2: LCMS: 0.86 min, 413 (M+1), mp: 187-188° C.

Example P6

Preparation of 4-(ethoxyamino)-6-[1-(3-pyridyl)pyrazol-4-yl]-1H-1,5-naphthyridin-2-one (Compound 9.004)

Example P6.1

Preparation of ethyl 3-amino-6-bromo-pyridine-2-carboxylate

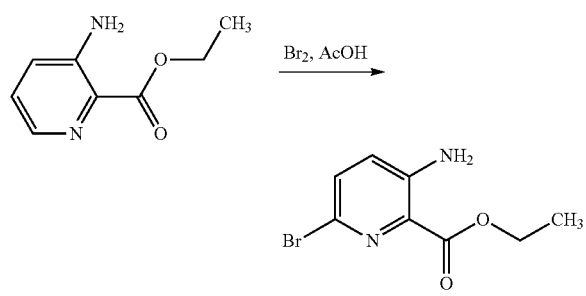

To a suspension of ethyl 3-aminopyridine-2-carboxylate (39.96 g, 241 mmol) in water (330 ml) was added H$_2$SO$_4$ (8 ml) and AcOH (16 ml). To this solution was added a solution of bromine in AcOH (84 ml) at ambient temperature under vigorous stirring so that the internal temperature remained around 25° C. After all bromine was added, stirring was continued for 1.5 h then the orange suspension was filtered giving ethyl 3-amino-6-bromo-pyridine-2-carboxylate.

LCMS: 0.76 min, 245, 247 (M+1) (Br isotope pattern).

Example P6.2

Preparation of ethyl 3-acetamido-6-bromo-pyridine-2-carboxylate

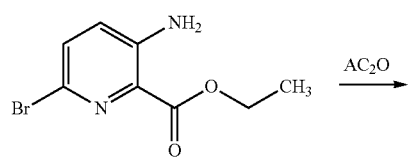

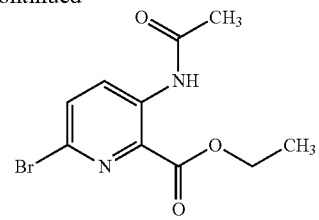

To a solution of ethy 3-amino-6-bromo-pyridine-2-carboxylate (10 g, 40.8 mmol) in THF (50 ml) was added Ac$_2$O (12 ml, 127.8 mmol) at ambient temperature then the solution was heated to 60° C. for 3 h. The solution was allowed to cool to ambient temperature then concentrated under reduced pressure and dissolved in ethyl acetate. This afforded the product in crystalline form. The mother liquor was purified using flash chromatography eluting with ethyl acetate/heptane, gradient, giving ethyl 3-acetamido-6-bromo-pyridine-2-carboxylate as a yellow solid.

LCMS: 0.82 min, 287, 289 (M+1) (Br isotope pattern).

Example P6.3

Preparation of 6-bromo-4-hydroxy-1H-1,5-naphthyridin-2-one

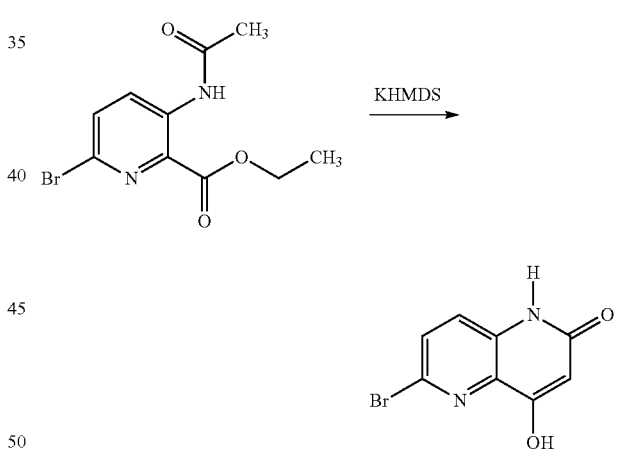

To a solution of KHMDS (0.5 M in toluene, 27 ml, 14 mmol) at −78° C. was slowly added a solution of ethyl 3-acetamido-6-bromo-pyridine-2-carboxylate (1.3 g, 4.5 mmol) in THF (20 ml). Stirring was continued for 1 h at this temperature then the cooling bath was removed. Ethyl acetate followed by water was added at ambient temperature, then the phases were separated. The yellow aqueous phase was treated with HCl (1 M) until a colorless solid was formed. Filtration and washing of the solid with water followed by drying afforded 6-bromo-4-hydroxy-1H-1,5-naphthyridin-2-one as a colorless solid. The compound is exclusively present in the tautomer shown.

LCMS: 0.46 min, 241, 243 (M+1) (Br isotope pattern).

Example P6.4

Preparation of 6-bromo-4-(ethoxyamino)-1H-1,5-naphthyridin-2-one

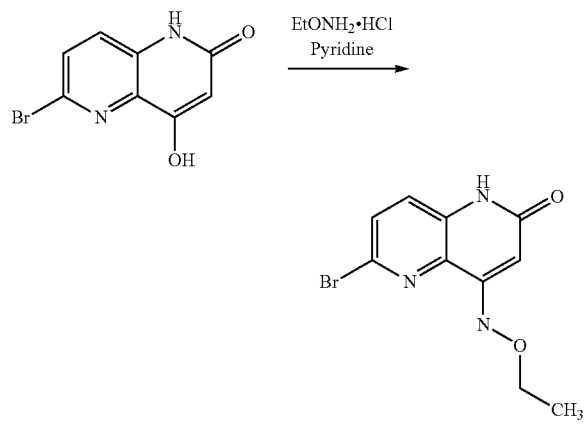

To a suspension of EtONH$_2$.HCl (1.05 g, 10.8 mmol) in pyridine (5 ml) was added 6-bromo-4-hydroxy-1H-1,5-naphthyridin-2-one (324 mg, 1.34 mmol) and stirring was continued for 17 h at 100° C. The mixture was allowed to cool to ambient temperature then water and ethyl acetate were added followed by separation of phases. The aqueous phase was extracted with ethyl acetate and the combined organic phases were dried over Na$_2$SO$_4$, filtered and concentrated in vacuo. Purification by flash chromatography eluting with ethyl acetate/MeOH, gradient, afforded 6-bromo-4-(ethoxyamino)-1H-1,5-naphthyridin-2-one.

LCMS: 0.73 min, 284, 286 (M+1) (Br isotope pattern). Mp: 229-230° C.

Example 6.5

Preparation of 4-(ethoxyamino)-6-[1-(3-pyridyl)pyrazol-4-yl]-1H-1,5-naphthyridin-2-one (Compound 9.004)

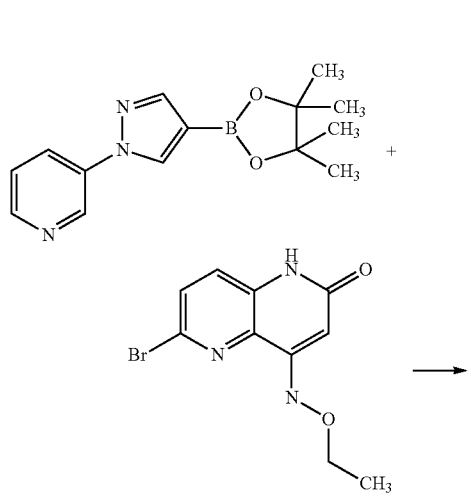

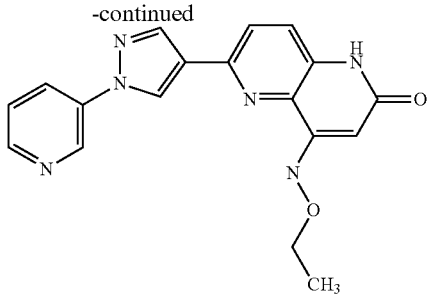

To Na$_2$CO$_3$ (151 mg, 1.41 mmol) was added water (1.5 ml) and acetonitrile (2 ml) and the solution was degassed for 5 min with argon. 3-[4-(4,4,5,5-tetramethyl-1,3,2-dioxaborolan-2-yl)pyrazol-1-yl]pyridine (84 mg, 0.31 mmol), 6-bromo-4-(ethoxyamino)-1H-1,5-naphthyridin-2-one (80 mg, 0.28 mmol) and Pd(dppf)Cl$_2$ (10 mg, 0.014 mmol) were added sequentially followed by addition of acetonitrile (2 ml). The mixture was stirred at 100° C. for 15 h then allowed to cool to ambient temperature. Water and ethyl acetate were added then the phases were separated. The aqueous phase was extracted with ethyl acetate, the combined organic phases were dried over Na$_2$SO$_4$, filtered and concentrated in vacuo. Purification by chromatography afforded of 4-(ethoxyamino)-6-[1-(3-pyridyl)pyrazol-4-yl]-1H-1,5-naphthyridin-2-one.

LCMS: 0.71 min, 349 (M+1)

Example P.7

Preparation of N-methoxy-6-[1-(3-pyridyl)pyrazol-4-yl]-2,3-dihydropyrano[3,2-b]pyridin-4-imine

Example P7.1

Preparation of 2,6-dibromopyridin-3-ol

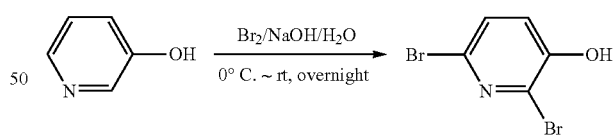

To a 3N aqueous NaOH solution (790 ml) was added bromine (40.7 ml, 0.789 mol) at 0° C. An ice cooled solution of pyridine-3-ol (25 g, 0.263 mol) in 150 ml 10% NaOH solution was then added slowly. The mixture was stirred at rt overnight. The mixture was filtered and the filtrate was acidified with conc. HCl to pH 2. The precipitate was filtered off, washed with H$_2$O, and dissolved in EtOAC (300 ml). The solution was dried MgSO$_4$ and concentrated in vacuum. The filtrate was purified from a silica column (petroleum/EtOAc, 3/1) to give the title compound as an off white solid.

$^1$H NMR (300 Mz, DMSO-d$^6$): δ 11.13 (s, 1H), 7.45 (d, J=9, 1H), 7.23 (d, J=7.5, 1H).

Example P7.2

Preparation of 2,6-dibromo-3-but-3-enoxy-pyridine

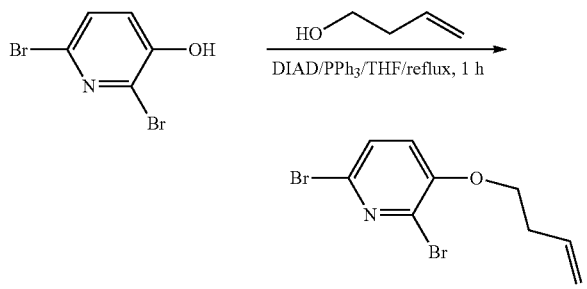

To a stirred mixture of 2,6-dibromopyridin-3-ol (47.3 g, 0.188 mol) and but-3-en-1-ol (13.8 g, 0.191 mol) in anhydrous THF (200 ml) at 0° C. was added PPh$_3$ (59.4 g, 0.226 mol), followed by diethyl azodicarboxylate (41.77 g, 0.207 mol). The mixture was heated at reflux for 1 h and then concentrated in vacuo to give a dark brown oil. The oil was dissolved in EtOAc, washed with saturated NaHCO$_3$ solution and brine, dried with Na$_2$SO$_4$, and concentrated in vacuo. Petroleum (300 ml) was added to the crude product mixture. The white solid was removed by filtration, and the filtrate was purified by silica gel chromatography (petroleum/EtOAc, 30/1) to afford the title compound as an oil.

$^1$H NMR (300 Mz, DMSO-d$^6$): δ 7.33 (d, J=9.3, 1H), 7.01 (d, J=7.2), 5.96-5.83 (m, 1H), 5.22-5.11 (m, 1H), 4.07-4.03 (t, J=6, 2H), 2.62-2.59 (m, 2H).

Example P7.3

Preparation of 6-bromo-4-methylene-2,3-dihydropyrano[3,2-b]pyridine

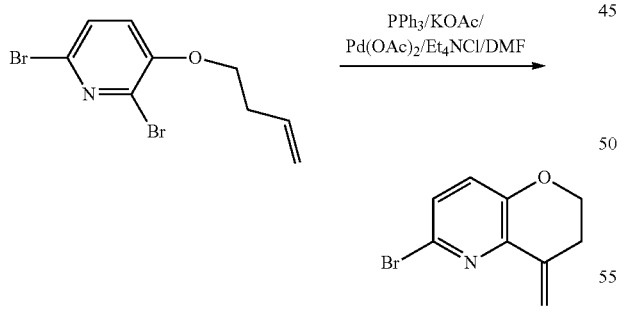

To a stirred mixture of PPh$_3$ (67.6 g, 0.258 mol), KOAc (42 g, 0.43 mol), Pd(OAc)$_2$ (1.94 g, 8.6 mmol) and Et$_4$NCl (28.6 g, 0.172 mmol), was added 2,6-dibromo-3-(but-3-enyloxy) pyridine (26.4 g, 0.086 mol) in anhydrous DMF (300 ml). The mixture was heated at 105° C. overnight. After cooling to rt, the mixture was dissolved in EtOAc, washed with water and brine, dried over Na$_2$SO$_4$, and concentrated in vacuo. The crude product was purified by silica gel chromatography (petroleum) to afford the title compound as an oil.

$^1$H NMR (300 Mz, DMSO-d$^6$): δ 7.40 (d, J=7.5, 1H), 7.24 (d, J=7.5, 1H), 5.98 (s, 1H), 5.12 (s, 1H), 4.20 (t, J=6, 2H), 2.74 (t, J=5.4, 2H).

Example P7.4

Preparation of 4-methylene-6-[1-(3-pyridyl)pyrazol-4-yl]-2,3-dihydropyrano[3,2-b]pyridine

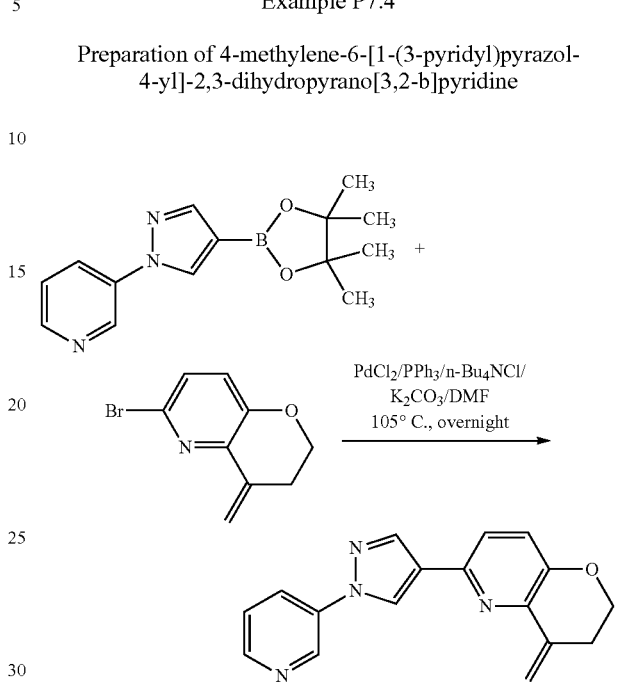

137 mg (0.78 mmol) of palladium chloride, 948 mg (3.62 mmol) of triphenylphosphine, 356 mg (25.8 mmol) of K$_2$CO$_3$ and 3.54 g (11.89 mmol) of n-Bu$_4$NCl in 30 ml of DMF were heated under 105° C. for 10 min under N$_2$. 3-[4-(4,4,5,5-tetramethyl-1,3,2-dioxaborolan-2-yl) pyrazol-1-yl]pyridine (3.5 g, 12.92 mmol) and 6-bromo-4-methylene-2,3-dihydropyrano[3,2-b]pyridine (3.2 g, 14.16 mmol) in DMF (20 ml) were added to the above solution and stirred overnight. EtOAc and water were added to the reaction mixture. The aqueous phase was extracted with EtOAc for 3 times, the combined organic phase was washed with water for 3 times, dried over Na$_2$SO$_4$, and concentrated in vacuum. The crude product was purified by silica gel chromatography (petroleum/EtOAc=1/1) to get the title compound as red solid.

$^1$H NMR (300 MHz, CDCl$_3$): δ 9.04 (d, 1H), 8.54 (d, 1H), 8.43 (s, 1H), 8.16 (s, 1H), 8.10-8.08 (m, 1H), 7.42-7.34 (m, 2H), 7.16 (d, J=8.4 Hz, 1H), 6.34 (s, 1H), 5.10 (s, 1H), 4.25 (t, J=5.7 Hz, 2H), 2.82 (t, J=5.7 Hz, 2H).

Example P7.5

Preparation of 6-[1-(3-pyridyl)pyrazol-4-yl]-2,3-dihydropyrano[3,2-b]pyridin-4-one

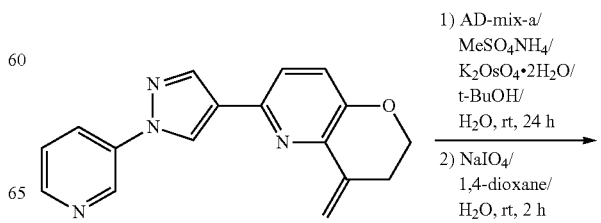

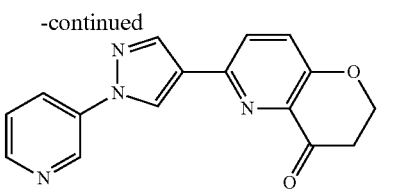

AD-mix-a (13.9 g, 1.44 g/mmol) was added to t-BuOH/H$_2$O (45 ml/45 ml), stirred at rt for 5 min. MeSO$_2$NH$_2$ (936 mg, 9.85 mmol) and K$_2$OsO$_4$.2H$_2$O (21 mg, 0.058 mmol) was added to the reaction mixture. The mixture was then cooled with ice, 4-methylene-6-[1-(3-pyridyl) pyrazol-4-yl]-2,3-dihydropyrano[3,2-b]pyridine (2.8 g, 9.66 mmol) in THF (25 ml) was added slowly to the above solution. Sodium sulfite (22 g, 2.25 g/mmol) was then added. After stirring for 15 min at 0° C., the ice bath was removed and the reaction mixture was stirred at rt for 45 min. The mixture was diluted with DCM (100 ml) and H$_2$O (100 ml) and the two layers were separated. The organic layer was washed with brine, dried over Na$_2$SO$_4$, filtered and concentrated, which was used directly for the next step. The crude product was dissolved in a 1:1 mixture of dioxane (30 ml) and H$_2$O (30 ml), and sodium periodate (1.9 g, 9.26 mmol) was added. The reaction mixture was stirred at rt for 1 h. The reaction mixture was diluted with DCM (50 ml) and H$_2$O (50 ml) and the two layers were separated. The organic layer was dried over Na$_2$SO$_4$, filtered and concentrated. The resulting residue was purified by silica gel chromatography (EtOAc/MeOH, 50/1) to afford the title compound as red solid.

$^1$H NMR (300 MHz, DMSO-d$^6$): 9.17-9.14 (m, 2H), 8.55-8.53 (m, 1H), 8.32-8.29 (m, 2H), 7.96 (d, J=9 Hz, 1H), 7.64-7.54 (m, 2H), 4.61 (t, J=6 Hz, 2H), 2.91 (t, J=6.6 Hz, 2H).

Example P7.6

Preparation of N-methoxy-6-[1-(3-pyridyl)pyrazol-4-yl]-2,3-dihydropyrano[3,2-b]pyridin-4-imine

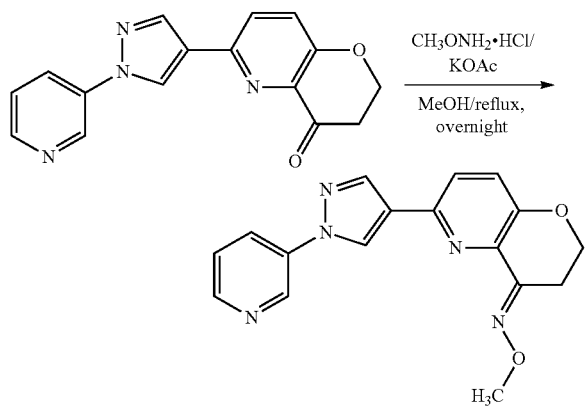

6-[1-(3-Pyridyl)pyrazol-4-yl]-2,3-dihydropyrano[3,2-b]pyridin-4-one (120 mg, 0.41 mmol), CH$_3$ONH$_2$.HCl (38 mg, 0.82 mmol) and KOAc (81 mg, 0.82 mmol) were suspended in methanol (3 ml) under N$_2$. The reaction mixture was refluxed overnight and purified by chromatography on silica (EtOAc) to get the title compound as a yellow solid.

$^1$H NMR (300 MHz, CDCl$_3$): 9.09 (s, 1H), 8.60-8.56 (m, 2H), 8.18-8.12 (m, 2H), 7.52-7.42 (m, 2H), 7.31-7.25 (m, 2H), 4.29 (t, J=6 Hz, 2H), 4.15 (s, 3H), 3.06 (t, J=6 Hz, 2H). ESI-MS(+): 322 (M+H)$^+$, 344 (M+Na)$^+$, 665 (2M+Na)$^+$.

Example P8

Preparation of N-methoxy-2-[1-(3-pyridyl)pyrazol-4-yl]-6,7-dihydro-5H-1,3-benzothiazol-4-imine Example P8.1

Preparation of 1-(3-pyridyl)pyrazole-4-carbothioamide

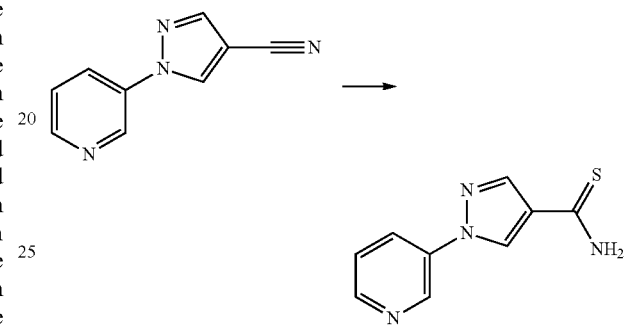

1-(3-pyridyl)pyrazole-4-carbonitrile (3.00 mmol, 0.511 g, described in WO2011/045240) was suspended in acetonitrile (3.00 ml) and hydrogen sulfide was bubbled through the reaction mixture for 10 min. The flask was closed and the saturated reaction mixture was heated to 60° C. After 1 h, the precipitated solid was filtered to yield the title compound as a solid.

LCMS: 0.47 min, 205 (M+1), mp: 244-7° C.

Example P8.2

Preparation of 2-[1-(3-pyridyl)pyrazol-4-yl]-6,7-dihydro-5H-1,3-benzothiazol-4-one

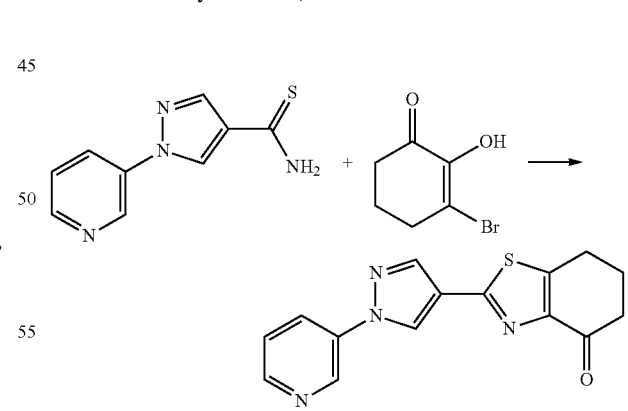

1-(3-pyridyl)pyrazole-4-carbothioamide (2.50 mmol, 0.510 g) and 3-bromo-2-hydroxy-cyclohex-2-en-1-one (2.50 mmol, 0.477 g, described in Tet. Lett. 2011, 52, 3633) were suspended in 10 ml acetic acid and the reaction mixture heated to reflux for 20 h. The reaction was cooled down to room temperature, diluted with water, slowly neutralised by dropwise addition in a saturated NaHCO$_3$ solution, and the aqueous phase was extracted with DCM. The combined organic phases were dried over $Na_2SO_4$, filtered and concentrated. The crude material was purified by Combiflash to give a solid which was crystallized in diethylether to yield the title compound as a light yellow solid.

LCMS: 0.71 min, 297 (M+1), mp: 162-165° C.

Example P8.3

Preparation of N-methoxy-2-[1-(3-pyridyl)pyrazol-4-yl]-6,7-dihydro-5H-1,3-benzothiazol-4-imine

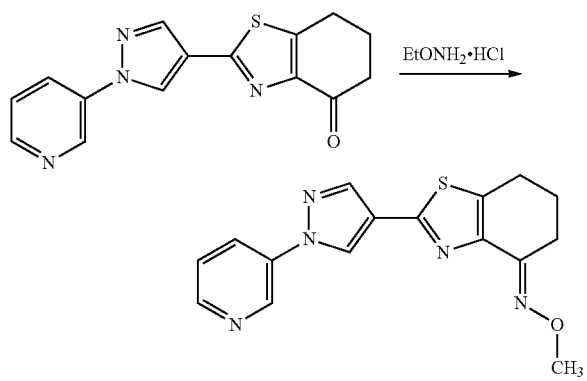

2-[1-(3-pyridyl)pyrazol-4-yl]-6,7-dihydro-5H-1,3-benzothiazol-4-one (0.40 mmol, 0.119 g) was suspended in 4 ml THF, and O-methylhydroxylamine hydrochloride (0.44 mmol, 0.0367 g) followed by sodium acetate (0.80 mmol, 0.0656 g) were added. The reaction mixture was heated at reflux. After evaporation of the solvent, the residue was submitted to chromatography (Combiflash) to yield the title compound as a yellow solid.

LCMS: 0.89 min, 326 (M+1), mp=141-143° C.

TABLE 1

Examples of compounds of formula (Iaa)

Formula Iaa

| Comp. No. | $R_{26}$ | $R_{20}$ | Xq | Phys. Data |
|---|---|---|---|---|
| 1.001 | H | H | $CH_2$ | Mp: >250° C. LCMS: 0.72 min, 306 (M + 1) |
| 1.002 | H | $CH_3$ | $CH_2$ | mp: 110-112° C. LCMS: 0.86 min, 320 (M + 1) |
| 1.003 | H | $CH_3CH_2$ | $CH_2$ | mp: 112-114° C. LCMS: 0.93 min, 334 (M + 1) |
| 1.004 | H | $CH_3CH_2CH_2$ | $CH_2$ | mp: 116-118° C. |
| 1.005 | H | $(CH_3)_2CH$ | $CH_2$ | mp: 128-130° C. LCMS: 1.00 min, 348 (M + 1) |
| 1.006 | H | $CH_2C=CH_2$ | $CH_2$ | mp: 129-131° C. LCMS: 0.96 min, 346 (M + 1) |
| 1.007 | H | H | O | mp: >250° C. $^1$H NMR (300 MHz, $d_6$-DMSO): 11.69 (s, 1H), 9.14-9.13 (m, 1H), 9.07 (s, 1H), 8.54-8.52 (m, 1H), 8.29-8.24 (m, 1H), 8.23 (s, 1H), 7.72 (d, J = 8.7 Hz, 1H), 7.58-7.53 (m, 1H), 7.41 (d, J = 8.7 Hz, 1H), 4.26-4.22 (m, 2H), 2.96-2.92 (m, 2H). |
| 1.008 | H | $CH_3$ | O | mp: 113-116° C. |
| 1.009 | H | $CH_3CH_2$ | O | mp: 107-108° C. |
| 1.010 | H | $CH_3CH_2CH_2$ | O | |
| 1.011 | H | $(CH_3)_2CH$ | O | mp: 127-128° C. |
| 1.012 | H | $CH_2C=CH_2$ | O | mp: 143-144° C. |
| 1.013 | H | H | $N-CH_3$ | |
| 1.014 | H | $CH_3$ | $N-CH_3$ | |
| 1.015 | H | $CH_3CH_2$ | $N-CH_3$ | |
| 1.016 | H | $CH_3CH_2CH_2$ | $N-CH_3$ | |
| 1.017 | H | $(CH_3)_2CH$ | $N-CH_3$ | |
| 1.018 | H | $CH_2C=CH_2$ | $N-CH_3$ | |
| 1.019 | H | H | $N-SO_2CH_3$ | |
| 1.020 | H | $CH_3$ | $N-SO_2CH_3$ | |
| 1.021 | H | $CH_3CH_2$ | $N-SO_2CH_3$ | |
| 1.022 | H | $CH_3CH_2CH_2$ | $N-SO_2CH_3$ | |
| 1.023 | H | $(CH_3)_2CH$ | $N-SO_2CH_3$ | |
| 1.024 | H | $CH_2C=CH_2$ | $N-SO_2CH_3$ | |
| 1.025 | $CH_3$ | $CH_2$-cyclopropyl | $CH_2$ | mp: 140-142° C. |
| 1.026 | $CH_3$ | $CH_3$ | $CH_2$ | mp: 128-130° C. |
| 1.027 | $CH_3$ | $CH_3CH_2$ | $CH_2$ | mp: 155-156° C. |
| 1.028 | $CH_3$ | $CH_2CCH$ | $CH_2$ | mp: 130-140° C. |
| 1.029 | $CH_3$ | $CH_2CH=CHCl$ | $CH_2$ | mp: 135-138° C. |
| 1.030 | $CH_3$ | $CH_2C=CH_2$ | $CH_2$ | mp: 111-114° C. |
| 1.031 | $CH_3$ | H | O | |
| 1.032 | $CH_3$ | $CH_3$ | O | |
| 1.033 | $CH_3$ | $CH_3CH_2$ | O | |
| 1.034 | $CH_3$ | $CH_3CH_2CH_2$ | O | |
| 1.035 | $CH_3$ | $(CH_3)_2CH$ | O | |
| 1.036 | $CH_3$ | $CH_2C=CH_2$ | O | |
| 1.037 | $CH_3$ | H | $N-CH_3$ | |
| 1.038 | $CH_3$ | $CH_3$ | $N-CH_3$ | |
| 1.039 | $CH_3$ | $CH_3CH_2CH_2$ | $N-CH_3$ | |
| 1.040 | $CH_3$ | $CH_3CH_2CH_2$ | $N-CH_3$ | |
| 1.041 | $CH_3$ | $(CH_3)_2CH$ | $N-CH_3$ | |
| 1.042 | $CH_3$ | $CH_2C=CH_2$ | $N-CH_3$ | |
| 1.043 | $CH_3$ | H | $N-SO_2CH_3$ | |
| 1.044 | $CH_3$ | $CH_3$ | $N-SO_2CH_3$ | |
| 1.045 | $CH_3$ | $CH_3CH_2$ | $N-SO_2CH_3$ | |
| 1.046 | $CH_3$ | $CH_3CH_2CH_2$ | $N-SO_2CH_3$ | |

TABLE 1-continued

Examples of compounds of formula (Iaa)

Formula Iaa

| Comp. No. | $R_{26}$ | $R_{20}$ | Xq | Phys. Data |
|---|---|---|---|---|
| 1.047 | $CH_3$ | $(CH_3)_2CH$ | $N-SO_2CH_3$ | |
| 1.048 | $CH_3$ | $CH_2C=CH_2$ | $N-SO_2CH_3$ | |

TABLE 2

Examples of compounds of formula (Ibb)

Formula Ibb

| Compound No. | $R_{26}$ | $R_{20}$ | Xq | Phys. Data |
|---|---|---|---|---|
| 2.001 | H | H | $CH_2$ | |
| 2.002 | H | $CH_3$ | $CH_2$ | |
| 2.003 | H | $CH_3CH_2$ | $CH_2$ | |
| 2.004 | H | $CH_3CH_2CH_2$ | $CH_2$ | |
| 2.005 | H | $(CH_3)_2CH$ | $CH_2$ | |
| 2.006 | H | $CH_2C=CH_2$ | $CH_2$ | |
| 2.007 | H | H | O | |
| 2.008 | H | $CH_3$ | O | |
| 2.009 | H | $CH_3CH_2$ | O | |
| 2.010 | H | $CH_3CH_2CH_2$ | O | |
| 2.011 | H | $(CH_3)_2CH$ | O | |
| 2.012 | H | $CH_2C=CH_2$ | O | |
| 2.013 | H | H | $N-CH_3$ | |
| 2.014 | H | $CH_3$ | $N-CH_3$ | |
| 2.015 | H | $CH_3CH_2$ | $N-CH_3$ | |
| 2.016 | H | $CH_3CH_2CH_2$ | $N-CH_3$ | |
| 2.017 | H | $(CH_3)_2CH$ | $N-CH_3$ | |
| 2.018 | H | $CH_2C=CH_2$ | $N-CH_3$ | |
| 2.019 | H | H | $N-SO_2CH_3$ | |
| 2.020 | H | $CH_3$ | $N-SO_2CH_3$ | |
| 2.021 | H | $CH_3CH_2$ | $N-SO_2CH_3$ | |
| 2.022 | H | $CH_3CH_2CH_2$ | $N-SO_2CH_3$ | |
| 2.023 | H | $(CH_3)_2CH$ | $N-SO_2CH_3$ | |
| 2.024 | H | $CH_2C=CH_2$ | $N-SO_2CH_3$ | |
| 2.025 | $CH_3$ | H | $CH_2$ | |
| 2.026 | $CH_3$ | $CH_3$ | $CH_2$ | |
| 2.027 | $CH_3$ | $CH_3CH_2$ | $CH_2$ | |
| 2.028 | $CH_3$ | $CH_3CH_2CH_2$ | $CH_2$ | |
| 2.029 | $CH_3$ | $(CH_3)_2CH$ | $CH_2$ | |
| 2.030 | $CH_3$ | $CH_2C=CH_2$ | $CH_2$ | |
| 2.031 | $CH_3$ | H | O | |
| 2.032 | $CH_3$ | $CH_3$ | O | |
| 2.033 | $CH_3$ | $CH_3CH_2$ | O | |
| 2.034 | $CH_3$ | $CH_3CH_2CH_2$ | O | |
| 2.035 | $CH_3$ | $(CH_3)_2CH$ | O | |
| 2.036 | $CH_3$ | $CH_2C=CH_2$ | O | |
| 2.037 | $CH_3$ | H | $N-CH_3$ | |
| 2.038 | $CH_3$ | $CH_3$ | $N-CH_3$ | |
| 2.039 | $CH_3$ | $CH_3CH_2$ | $N-CH_3$ | |
| 2.040 | $CH_3$ | $CH_3CH_2CH_2$ | $N-CH_3$ | |
| 2.041 | $CH_3$ | $(CH_3)_2CH$ | $N-CH_3$ | |
| 2.042 | $CH_3$ | $CH_2C=CH_2$ | $N-CH_3$ | |
| 2.043 | $CH_3$ | H | $N-SO_2CH_3$ | |
| 2.044 | $CH_3$ | $CH_3$ | $N-SO_2CH_3$ | |
| 2.045 | $CH_3$ | $CH_3CH_2$ | $N-SO_2CH_3$ | |
| 2.046 | $CH_3$ | $CH_3CH_2CH_2$ | $N-SO_2CH_3$ | |
| 2.047 | $CH_3$ | $(CH_3)_2CH$ | $N-SO_2CH_3$ | |
| 2.048 | $CH_3$ | $CH_2C=CH_2$ | $N-SO_2CH_3$ | |

TABLE 3

Examples of compounds of formula (Icc)

Formula Icc

| Compound No. | $R_{26}$ | $R_{20}$ | Xq | Phys. Data |
|---|---|---|---|---|
| 3.001 | H | H | $CH_2$ | mp: 162-5° C. |
| 3.002 | H | $CH_3$ | $CH_2$ | mp: 141-3° C. |
| 3.003 | H | $CH_3CH_2$ | $CH_2$ | mp: 142-4° C. |
| 3.004 | H | $CH_3CH_2CH_2$ | $CH_2$ | |
| 3.005 | H | $(CH_3)_2CH$ | $CH_2$ | |
| 3.006 | H | $CH_2C=CH_2$ | $CH_2$ | |
| 3.007 | H | H | O | |
| 3.008 | H | $CH_3$ | O | |
| 3.009 | H | $CH_3CH_2$ | O | |
| 3.010 | H | $CH_3CH_2CH_2$ | O | |
| 3.011 | H | $(CH_3)_2CH$ | O | |
| 3.012 | H | $CH_2C=CH_2$ | O | |
| 3.013 | H | H | $N-CH_3$ | |
| 3.014 | H | $CH_3$ | $N-CH_3$ | |
| 3.015 | H | $CH_3CH_2$ | $N-CH_3$ | |
| 3.016 | H | $CH_3CH_2CH_2$ | $N-CH_3$ | |
| 3.017 | H | $(CH_3)_2CH$ | $N-CH_3$ | |
| 3.018 | H | $CH_2C=CH_2$ | $N-CH_3$ | |
| 3.019 | H | H | $N-SO_2CH_3$ | |
| 3.020 | H | $CH_3$ | $N-SO_2CH_3$ | |

TABLE 3-continued

Examples of compounds of formula (Icc)

Formula Icc

| Compound No. | $R_{26}$ | $R_{20}$ | Xq | Phys. Data |
|---|---|---|---|---|
| 3.021 | H | $CH_3CH_2$ | $N-SO_2CH_3$ | |
| 3.022 | H | $CH_3CH_2CH_2$ | $N-SO_2CH_3$ | |
| 3.023 | H | $(CH_3)_2CH$ | $N-SO_2CH_3$ | |
| 3.024 | H | $CH_2C=CH_2$ | $N-SO_2CH_3$ | |
| 3.025 | $CH_3$ | H | $CH_2$ | |
| 3.026 | $CH_3$ | $CH_3$ | $CH_2$ | |
| 3.027 | $CH_3$ | $CH_3CH_2$ | $CH_2$ | |
| 3.028 | $CH_3$ | $CH_3CH_2CH_2$ | $CH_2$ | |
| 3.029 | $CH_3$ | $(CH_3)_2CH$ | $CH_2$ | |
| 3.030 | $CH_3$ | $CH_2C=CH_2$ | $CH_2$ | |
| 3.031 | $CH_3$ | H | O | |
| 3.032 | $CH_3$ | $CH_3$ | O | |
| 3.033 | $CH_3$ | $CH_3CH_2$ | O | |
| 3.034 | $CH_3$ | $CH_3CH_2CH_2$ | O | |
| 3.035 | $CH_3$ | $(CH_3)_2CH$ | O | |
| 3.036 | $CH_3$ | $CH_2C=CH_2$ | O | |
| 3.037 | $CH_3$ | H | $N-CH_3$ | |
| 3.038 | $CH_3$ | $CH_3$ | $N-CH_3$ | |
| 3.039 | $CH_3$ | $CH_3CH_2$ | $N-CH_3$ | |
| 3.040 | $CH_3$ | $CH_3CH_2CH_2$ | $N-CH_3$ | |
| 3.041 | $CH_3$ | $(CH_3)_2CH$ | $N-CH_3$ | |
| 3.042 | $CH_3$ | $CH_2C=CH_2$ | $N-CH_3$ | |
| 3.043 | $CH_3$ | H | $N-SO_2CH_3$ | |
| 3.044 | $CH_3$ | $CH_3$ | $N-SO_2CH_3$ | |
| 3.045 | $CH_3$ | $CH_3CH_2$ | $N-SO_2CH_3$ | |
| 3.046 | $CH_3$ | $CH_3CH_2CH$ | $2 N-SO_2CH_3$ | |
| 3.047 | $CH_3$ | $(CH_3)_2CH$ | $N-SO_2CH_3$ | |
| 3.048 | $CH_3$ | $CH_2C=CH_2$ | $N-SO_2CH_3$ | |

TABLE 4

Examples of compounds of formula (Idd)

Formula Idd

| Compound No. | $R_{26}$ | $R_{20}$ | Xq | Phys. Data |
|---|---|---|---|---|
| 4.001 | H | H | $CH_2$ | |
| 4.002 | H | $CH_3$ | $CH_2$ | |
| 4.003 | H | $CH_3CH_2$ | $CH_2$ | |
| 4.004 | H | $CH_3CH_2CH_2$ | $CH_2$ | |
| 4.005 | H | $(CH_3)_2CH$ | $CH_2$ | |
| 4.006 | H | $CH_2C=CH_2$ | $CH_2$ | |
| 4.007 | H | H | O | |
| 4.008 | H | $CH_3$ | O | |
| 4.009 | H | $CH_3CH_2$ | O | |
| 4.01 | H | $CH_3CH_2CH_2$ | O | |
| 4.011 | H | $(CH_3)_2CH$ | O | |
| 4.012 | H | $CH_2C=CH_2$ | O | |
| 4.013 | H | H | $N-CH_3$ | |
| 4.014 | H | $CH_3$ | $N-CH_3$ | |
| 4.015 | H | $CH_3CH_2$ | $N-CH_3$ | |
| 4.016 | H | $CH_3CH_2CH_2$ | $N-CH_3$ | |
| 4.017 | H | $(CH_3)_2CH$ | $N-CH_3$ | |
| 4.018 | H | $CH_2C=CH_2$ | $N-CH_3$ | |
| 4.019 | H | H | $N-SO_2CH_3$ | |
| 4.020 | H | $CH_3$ | $N-SO_2CH_3$ | |
| 4.021 | H | $CH_3CH_2$ | $N-SO_2CH_3$ | |
| 4.022 | H | $CH_3CH_2CH_2$ | $N-SO_2CH_3$ | |
| 4.023 | H | $(CH_3)_2CH$ | $N-SO_2CH_3$ | |
| 4.024 | H | $CH_2C=CH_2$ | $N-SO_2CH_3$ | |
| 4.025 | $CH_3$ | H | $CH_2$ | |
| 4.026 | $CH_3$ | $CH_3$ | $CH_2$ | |
| 4.027 | $CH_3$ | $CH_3CH_2$ | $CH_2$ | |
| 4.028 | $CH_3$ | $CH_3CH_2CH_2$ | $CH_2$ | |
| 4.029 | $CH_3$ | $(CH_3)_2CH$ | $CH_2$ | |
| 4.030 | $CH_3$ | $CH_2C=CH_2$ | $CH_2$ | |
| 4.031 | $CH_3$ | H | O | |
| 4.032 | $CH_3$ | $CH_3$ | O | |
| 4.033 | $CH_3$ | $CH_3CH_2$ | O | |
| 4.034 | $CH_3$ | $CH_3CH_2CH_2$ | O | |
| 4.035 | $CH_3$ | $(CH_3)_2CH$ | O | |
| 4.036 | $CH_3$ | $CH_2C=CH_2$ | O | |
| 4.037 | $CH_3$ | H | $N-CH_3$ | |
| 4.038 | $CH_3$ | $CH_3$ | $N-CH_3$ | |
| 4.039 | $CH_3$ | $CH_3CH_2$ | $N-CH_3$ | |
| 4.040 | $CH_3$ | $CH_3CH_2CH_2$ | $N-CH_3$ | |
| 4.041 | $CH_3$ | $(CH_3)_2CH$ | $N-CH_3$ | |
| 4.042 | $CH_3$ | $CH_2C=CH_2$ | $N-CH_3$ | |
| 4.043 | $CH_3$ | H | $N-SO_2CH_3$ | |
| 4.044 | $CH_3$ | $CH_3$ | $N-SO_2CH_3$ | |
| 4.045 | $CH_3$ | $CH_3CH_2$ | $N-SO_2CH_3$ | |
| 4.046 | $CH_3$ | $CH_3CH_2CH_2$ | $N-SO_2CH_3$ | |
| 4.047 | $CH_3$ | $(CH_3)_2CH$ | $N-SO_2CH_3$ | |
| 4.048 | $CH_3$ | $CH_2C=CH_2$ | $N-SO_2CH_3$ | |

TABLE 5

Examples of compounds of formula (Iee)

Formula Iee

| Compound No. | R24 | R20 | Xq | Phys. Data |
|---|---|---|---|---|
| 5.001 | H | H | CH2 | |
| 5.002 | H | CH3 | CH2 | |
| 5.003 | H | CH3CH2 | CH2 | |
| 5.004 | H | CH3CH2CH2 | CH2 | |
| 5.005 | H | (CH3)2CH | CH2 | |
| 5.006 | H | CH2=CH2 | CH2 | |
| 5.007 | H | H | O | |
| 5.008 | H | CH3 | O | |
| 5.009 | H | CH3CH2 | O | |
| 5.01 | H | CH3CH2CH2 | O | |
| 5.011 | H | (CH3)2CH | O | |
| 5.012 | H | CH2=CH2 | O | |
| 5.013 | H | H | N—CH3 | |
| 5.014 | H | CH3 | N—CH3 | |
| 5.015 | H | CH3CH2 | N—CH3 | |
| 5.016 | H | CH3CH2CH2 | N—CH3 | |
| 5.017 | H | (CH3)2CH | N—CH3 | |
| 5.018 | H | CH2=CH2 | N—CH3 | |
| 5.019 | H | H | N—SO2CH3 | |
| 5.020 | H | CH3 | N—SO2CH3 | |
| 5.021 | H | CH3CH2 | N—SO2CH3 | |
| 5.022 | H | CH3CH2CH2 | N—SO2CH3 | |
| 5.023 | H | (CH3)2CH | N—SO2CH3 | |
| 5.024 | H | CH2=CH2 | N—SO2CH3 | |
| 5.025 | CH3 | H | CH2 | |
| 5.026 | CH3 | CH3 | CH2 | |
| 5.027 | CH3 | CH3CH2 | CH2 | |
| 5.028 | CH3 | CH3CH2CH2 | CH2 | |
| 5.029 | CH3 | (CH3)2CH | CH2 | |
| 5.030 | CH3 | CH2=CH2 | CH2 | |
| 5.031 | CH3 | H | O | |
| 5.032 | CH3 | CH3 | O | |
| 5.033 | CH3 | CH3CH2 | O | |
| 5.034 | CH3 | CH3CH2CH2 | O | |
| 5.035 | CH3 | (CH3)2CH | O | |
| 5.036 | CH3 | CH2=CH2 | O | |
| 5.037 | CH3 | H | N—CH3 | |
| 5.038 | CH3 | CH3 | N—CH3 | |
| 5.039 | CH3 | CH3CH2 | N—CH3 | |
| 5.040 | CH3 | CH3CH2CH2 | N—CH3 | |
| 5.041 | CH3 | (CH3)2CH | N—CH3 | |
| 5.042 | CH3 | CH2=CH2 | N—CH3 | |
| 5.043 | CH3 | H | N—SO2CH3 | |
| 5.044 | CH3 | CH3 | N—SO2CH3 | |
| 5.045 | CH3 | CH3CH2 | N—SO2CH3 | |
| 5.046 | CH3 | CH3CH2CH2 | N—SO2CH3 | |
| 5.047 | CH3 | (CH3)2CH | N—SO2CH3 | |
| 5.048 | CH3 | CH2=CH2 | N—SO2CH3 | |

TABLE 6

Examples of compounds of formula (Iff)

formula (Iff)

| Comp. No. | R26 | R20 | R21 | Xq | Phys. Data |
|---|---|---|---|---|---|
| 6.001 | H | H | H | CH2 | |
| 6.002 | H | CH3 | H | CH2 | |
| 6.003 | H | CH3 | CH3 | CH2 | LCMS: 0.61 min, 333 (M + 1) |
| 6.004 | H | H | CO2CH3 | CH2 | |
| 6.005 | H | CH3 | CO2CH3 | CH2 | |
| 6.006 | H | H | SO2CH3 | CH2 | |
| 6.007 | H | H | COCH3 | CH2 | mp: 190-191° C. LCMS: 0.89 min, 347 (M + 1) |
| 6.008 | CH3 | H | H | CH2 | |
| 6.009 | CH3 | CH3 | H | CH2 | |
| 6.010 | CH3 | CH3 | CH3 | CH2 | |
| 6.011 | CH3 | H | CO2CH3 | CH2 | |
| 6.012 | CH3 | CH3 | CO2CH3 | CH2 | |
| 6.013 | CH3 | H | SO2CH3 | CH2 | |
| 6.014 | CH3 | CH3 | SO2CH3 | CH2 | |
| 6.015 | H | H | H | O | |
| 6.016 | H | CH3 | H | O | mp: 127-128° C. |
| 6.017 | H | CH3 | CH3 | O | |
| 6.018 | H | H | CO2CH3 | O | mp: 242-243° C. |
| 6.019 | H | CH3 | CO2CH3 | O | $^1$H NMR (300 MHz, CDCl$_3$): 9.10-9.09 (m, 1H), 8.64-8.56 (m, 2H), 8.17-8.10 (m, 2H), 7.59 (d, J = 8.4 Hz, 1H), 7.46-7.43 (m, 1H), 7.33 (d, J = 8.4 Hz, 1H), 3.50 (t, J = 6 Hz, 2H), 3.76 (s, 3H), 3.41 (s, 3H), 2.96 (t, J = 6 Hz, 2H). |
| 6.020 | H | H | SO2CH3 | O | mp: >250° C. $^1$H NMR (300 MHz, d$_6$-DMSO): 15.14 (s, 1H), 9.21-9.20 (m, 1H), 8.62-8.60 (m, 1H), 8.55 (s, 1H), 8.15 (s, 1H), 8.14-8.12 (m, 1H), 7.62 (d, J = 8.4 Hz, 1H), 7.50-7.45 (m, 2H), 4.48-4.44 (m, 2H), 3.23 (s, 3H), 3.02-2.98 (m, 2H). |
| 6.021 | H | CH3 | SO2CH3 | O | |
| 6.022 | CH3 | H | H | N—CH3 | |
| 6.023 | CH3 | CH3 | H | N—CH3 | |
| 6.024 | CH3 | CH3 | CH3 | N—CH3 | |
| 6.025 | CH3 | H | CO2CH3 | N—CH3 | |
| 6.026 | CH3 | CH3 | CO2CH3 | N—CH3 | |
| 6.027 | CH3 | H | SO2CH3 | N—SO2CH3 | |
| 6.028 | CH3 | CH3 | SO2CH3 | N—SO2CH3 | |

TABLE 7

Examples of compounds of formula Igg (Igg)

| Comp. No. | $R_{26}$ | $G_1$ | $G_2$ | Xq | Phys. Data |
|---|---|---|---|---|---|
| 7.001 | $CH_3$ | CH | CH | $CH_2$ | |
| 7.002 | H | CH | CH | $CH_2$ | mp: 158-1.59° C. LCMS: 0.72 min, 291 (M + 1) |
| 7.003 | $CH_3$ | CH | CH | O | |
| 7.004 | H | CH | CH | O | $^1$H NMR (300 MHz, DMSO-$d^6$): 9.17-9.14 (m, 2H), 8.55-8.53 (m, 1H), 8.32-8.29 (m, 2H), 7.96 (d, J = 9 Hz, 1H), 7.64-7.54 (m, 2H), 4.61 (t, J = 6 Hz, 2H), 2.91 (t, J = 6.6 Hz, 2H) |
| 7.005 | $CH_3$ | CH | CH | NH | |
| 7.006 | H | CH | CH | NH | |
| 7.007 | $CH_3$ | CH | CH | N—$CH_3$ | |
| 7.008 | H | CH | CH | N—$CH_3$ | |
| 7.009 | $CH_3$ | CH | CH | $NSO_2CH_3$ | |
| 7.010 | H | CH | CH | $NSO_2CH_3$ | |

TABLE 8

Examples of compounds of formula Ihh:

(Ihh)

| Comp. No. | $R_{26}$ | $A_3$ | $Z_1$ | Phys. Data |
|---|---|---|---|---|
| 8.001 | H | $CH_2$ | O | LCMS: 0.70 min, 356 (M + 1) |
| 8.002 | H | $CH_2$ | $NOCH_3$ | mp: 181-5° C. |
| 8.003 | H | $CH_2$ | $NOCH_2CH_3$ | LCMS: 0.83 min, 399 (M + 1) |
| 8.004 | H | $C(CH_3)_2$ | $NOCH_3$ (isomer A) | mp: 197-9° C. |
| 8.005 | H | $C(CH_3)_2$ | $NOCH_3$ (isomer B) | mp: 187-8° C. |

TABLE 9

Further preferred compounds of formula I:

| Comp. No. | Structure | Phys. Data |
|---|---|---|
| 9.001 | 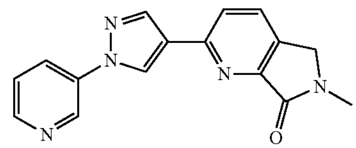 [SMILES: CN1Cc2ccc(-c3cnn(-c4cccnc4)c3)nc2C1=O] | mp: >240° C. LCMS: 0.60 min, 292 (M + 1) |
| 9.002 | 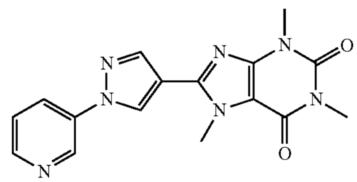 [SMILES: Cn1c(=O)c2c(nc(-c3cnn(-c4cccnc4)c3)n2C)n(C)c1=O] | Mp. >300° C. LCMS: 0.68 min, 338 (M + 1) |
| 9.003 | 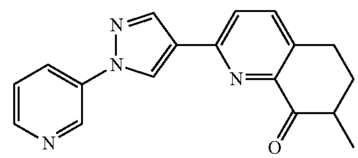 [SMILES: CC1CCc2ccc(-c3cnn(-c4cccnc4)c3)nc2C1=O] | LCMS: 0.79 min, 305 (M + 1) |
| 9.004 | 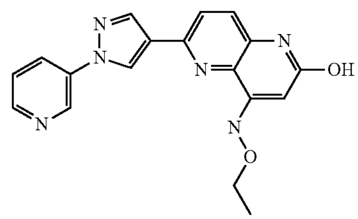 [SMILES: CCONc1cc(O)nc2ccc(-c3cnn(-c4cccnc4)c3)nc12] | LCMS: 0.73 min, 349 (M + 1) |
| 9.005 | 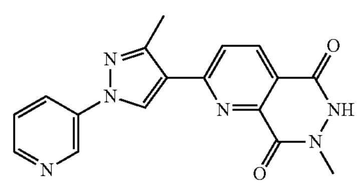 [SMILES: Cc1nn(-c2cccnc2)cc1-c1ccc2c(=O)[nH]n(C)c(=O)c2n1] | LCMS: 0.63 and 0.68 min, 335 (M + 1), mixture of 2 isomers |
| 9.006 | 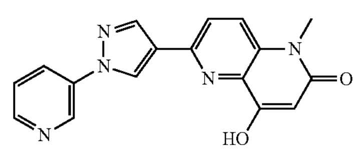 [SMILES: Cn1c(=O)cc(O)c2nc(-c3cnn(-c4cccnc4)c3)ccc21] | LCMS: 0.68 min, 320 (M + 1) |
| 9.007 | 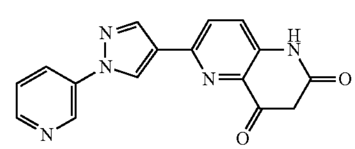 [SMILES: O=C1CC(=O)c2nc(-c3cnn(-c4cccnc4)c3)ccc2N1] | LCMS: 0.67 min, 306 (M + 1) |

$^1$H NMR Measurements: Measured on a Brucker 400 MHz spectrometer, chemical shifts given in ppm relevant to a TMS standard. Spectra measured in solvents indicated.

LCMS Methods:
LCMS 1:
LCMS. Spectra were recorded on a ACQUITY SQD Mass Spectrometer (Waters Corp. Milford, Mass., USA) mass spectrometer equipped with an electrospray source (ESI; source temperature 150° C.; desolvation temperature 200° C.; cone voltage 30 V; cone gas flow 0 L/h, desolvation gas flow 650 L/h, mass range: 100 to 900 Da) and a Waters ACQUITY UPLC (column: Phenomenex Gemini C18, 3 μm, 30×2 mm (Phenomenex, Torrance, Calif., USA)); column temperature: 60° C.; flow rate 0.85 ml/min; eluent A: Water/Methanol 95:5, 0.05% formic acid; eluent B: Acetonitrile, 0.05% formic acid; gradient: 0 min 100% A; 0-1.2 min 100% A; 1.2-1.5 min 100% B; UV-detection: 210-500 nm, resolution 2 nm. The flow was split postcolumn prior to MS analysis.

Formulation examples (% = percent by weight)

| Example F1: Emulsion concentrates | a) | b) | c) |
|---|---|---|---|
| Active ingredient | 25% | 40% | 50% |
| Calcium dodecylbenzenesulfonate | 5% | 8% | 6% |
| Castor oil polyethylene glycol ether (36 mol of EO) | 5% | — | — |
| Tributylphenoxypolyethylene glycol ether (30 mol of EO) | — | 12% | 0.04 |
| Cyclohexanone | — | 15% | 20% |
| Xylene mixture | 65% | 25% | 20% |

Emulsions of any desired concentration can be prepared from such concentrates by dilution with water.

| Example F2: Solutions | a) | b) | c) | d) |
|---|---|---|---|---|
| Active ingredient | 80% | 10% | 5% | 95% |
| Ethylene glycol monomethyl ether | 20% | — | — | — |
| Polyethylene glycol MW 400 | — | 70% | — | — |
| N-Methylpyrrolid-2-one | — | 20% | — | — |
| Epoxidized coconut oil | — | — | 1% | 5% |
| Petroleum ether (boiling range: 160-190°) | — | — | 94% | — |

The solutions are suitable for use in the form of microdrops.

| Example F3: Granules | a) | b) | c) | d) |
|---|---|---|---|---|
| Active ingredient | 5% | 10% | 8% | 21% |
| Kaolin | 94% | — | 79% | 54% |
| Highly disperse silica | 1% | — | 13% | 7% |
| Attapulgite | — | 90% | — | 18% |

The active ingredient is dissolved in dichloromethane, the solution is sprayed onto the carrier(s), and the solvent is subsequently evaporated in vacuo.

| Example F4: Dusts | a) | b) |
|---|---|---|
| Active ingredient | 2% | 5% |
| Highly disperse silica | 1% | 5% |
| Talc | 97% | — |
| Kaolin | — | 90% |

Ready-to-use dusts are obtained by intimately mixing the carriers and the active ingredient.

| Example F5: Wettable powders | a) | b) | c) |
|---|---|---|---|
| Active ingredient | 25% | 50% | 75% |
| Sodium lignosulfonate | 5% | 5% | — |
| Sodium lauryl sulfate | 3% | — | 5% |
| Sodium diisobutyl-naphthalenesulfonate | — | 6% | 10% |
| Octylphenoxypolyethylene glycol ether (7-8 mol of EO) | — | 2% | — |
| Highly disperse silica | 5% | 10% | 10% |
| Kaolin | 62% | 27% | — |

The active ingredient is mixed with the additives and the mixture is ground thoroughly in a suitable mill. This gives wettable powders, which can be diluted with water to give suspensions of any desired concentration.

| Example F6: Extruder granules | |
|---|---|
| Active ingredient | 10% |
| Sodium lignosulfonate | 2% |
| Carboxymethylcellulose | 1% |
| Kaolin | 87% |

The active ingredient is mixed with the additives, and the mixture is ground, moistened with water, extruded, granulated and dried in a stream of air.

| Example F7: Coated granules | |
|---|---|
| Active ingredient | 3% |
| Polyethylene glycol (MW 200) | 3% |
| Kaolin | 94% |

In a mixer, the finely ground active ingredient is applied uniformLy to the kaolin, which has been moistened with the polyethylene glycol. This gives dust-free coated granules.

| Example F8: Suspension concentrate | |
|---|---|
| Active ingredient | 40% |
| Ethylene glycol | 10% |
| Nonylphenoxypolyethylene glycol ether (15 mol of EO) | 6% |
| Sodium lignosulfonate | 10% |
| Carboxymethylcellulose | 1% |
| 37% aqueous formaldehyde solution | 0.2% |
| Silicone oil (75% aqueous emulsion) | 0.8% |
| Water | 32% |

The finely ground active ingredient is mixed intimately with the additives. Suspensions of any desired concentration can be prepared from the thus resulting suspension concentrate by dilution with water.

| Example F9: Powders for dry seed treatment | a) | b) | c) |
|---|---|---|---|
| active ingredient | 25% | 50% | 75% |
| light mineral oil | 5% | 5% | 5% |
| highly dispersed silicic acid | 5% | 5% | — |
| Kaolin | 65% | 40% | — |
| Talcum | — | — | 20% |

The combination is thoroughly mixed with the adjuvants and the mixture is thoroughly ground in a suitable mill, affording powders that can be used directly for seed treatment.

Example F10: Emulsifiable concentrate

| | |
|---|---|
| active ingredient | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

Example F11: Flowable concentrate for seed treatment

| | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridyl-methyleneamino derivatives, macrolides, neonicotinoids and *Bacillus thuringiensis* preparations.

The following mixtures of the compounds of formula I with active ingredients are preferred (the abbreviation "TX" means "one compound selected from the group consisting of the compounds described in Tables 1 to 7 of the present invention"):

an adjuvant selected from the group of substances consisting of petroleum oils (alternative name) (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate (alternative name)+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/ Chemical Abstracts name) (1216)+TX, hexythiazox (441)+TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfiram (alternative name) [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dacty-*

*lopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure $B_1$ (alternative name) (839)+TX, trimedlure $B_2$ (alternative name) (839)+TX, trimedlure C (alternative name) (839) and trunc-call (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxyl)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl 0-(methoxyaminothiophosphoryl)salicylate (IUPAC name)

(473)+TX, isoprothiolane (474)+TX, isothioate (1244)+TX, isoxathion (480)+TX, ivermectin (alternative name) [CCN]+TX, jasmolin I (696)+TX, jasmolin II (696)+TX, jodfenphos (1248)+TX, juvenile hormone I (alternative name) [CCN]+TX, juvenile hormone II (alternative name) [CCN]+TX, juvenile hormone III (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene III (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name)+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoro-acetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropimorph [67306-00-7]+TX, fenpropidine [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-L190 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfo-carb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (disclosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12b-trimethyl-11-oxo-9-(3-pyridinyl)-2H,11Hnaphtho [2,1-b]pyrano [3,4-e]pyran-4-yl]methyl-cyclopropanecarboxylate [915972-17-7]+TX and 1,3,5-trimethyl-N-(2-methyl-1-oxopropyl)-N-[3-(2-methylpropyl)-4-[2,2,2-trifluoro-1-methoxy-1-(trifluoromethyl)ethyl]phenyl]-1H-pyrazole-4-carboxamide [926914-55-8]+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright © 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds of formula I selected from Tables 1-7 with active ingredients described above comprises a compound selected from Tables 1-7 and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on other hand, molar ratios.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I selected from Tables 1-7 and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Tables 1-7 and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula (I). Further, it is hereby made available, a composition comprising a plant propagation material treated with a compound of formula (I).

Seed treatment comprises all suitable seed treatment techniques known in the art, such as seed dressing, seed coating, seed dusting, seed soaking and seed pelleting. The seed treatment application of the compound formula (I) can be carried out by any known methods, such as spraying or by dusting the seeds before sowing or during the sowing/planting of the seeds.

BIOLOGICAL EXAMPLES

Example B1

Activity Against *Myzus persicae* (Green Peach Aphid)

(Mixed Population, Feeding/Residual Contact Activity, Preventive)

Sunflower leaf discs were placed on agar in a 24-well microtiter plate and sprayed with test solutions. After drying, the leaf discs were infested with an aphid population of mixed ages. After an incubation period of 6 days, samples were checked for mortality. In this test, compounds 1.002, 1.003, 1.004, 1.006, 1.008, 1.009, 1.011, 1.012, 1.025, 1.026, 1.027, 1.028, 1.029, 1.029, 1.030, 3.002, 3.003, 6.003, 6.007, 6.016, 6.019, 7.004, 8.002, 8.003, 8.004, 8.005, 9.001 and 9.003 showed an activity of over 80% at a concentration of 200 ppm.

Example B2

Activity Against *Bemisia tabaci* (Cotton White Fly)

(Feeding/Residual Contact Activity, Preventive)

Cotton leaf discs were placed on agar in a 24-well microtiter plate and sprayed with test solutions. After drying, the leaf discs were infested with 12 to 18 adults. After an incubation period of 6 days after infestation, samples were checked for mortality and special effects (e.g. phytotoxicity). In this test, compound 1.002, 1.003, 1.004, 1.008, 1.009, 1.011, 1.012, 1.025, 1.026, 1.027, 1.028, 1.029, 1.030, 6.003, 6.016, 6.019, 7.001, 7.002, 7.004, 8.002, 8.003, 8.004, 8.005 and 9.003 showed an activity of over 80% at a concentration of 200 ppm.

What is claimed is:

1. A compound of formula I

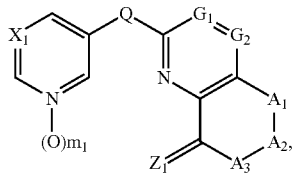

wherein
X$_1$ is nitrogen or CR$_1$;
G$_1$ is nitrogen or CR$_2$;
G$_2$ is nitrogen or CR$_3$;
or G$_1$-G$_2$ together is —S—, —O—, —NH—, or N—CH$_3$;
A$_1$ is oxygen, S(O)n$_1$, S(O)(=NR$_4$), C=O, NR$_5$, CR$_6$R$_7$, —CR$_8$CR$_9$— or a direct bond;
A$_2$ is oxygen, S(O)n$_2$, NR$_{10}$, C=O or CR$_{11}$R$_{12}$;
A$_3$ is oxygen, NR$_{13}$, CR$_{14}$R$_{15}$ or —CR$_{16}$CR$_{17}$—;
or A$_2$-A$_3$ together represents a group —CR$_{18}$=CR$_{19}$—;
with the provisos that;
  a) not more than 1 substituent A can be oxygen or sulfur;
  b) not more than 2 substituents A can be nitrogen;
  c) 2 substituents A as nitrogen can be adjacent to each other or separated by a sulfur or carbon substituent;
R$_1$ is hydrogen or halogen;
R$_2$ and R$_3$, independently from each other, are hydrogen, halogen, C$_1$-C$_3$alkyl or C$_1$-C$_3$haloalkyl;
R$_4$, R$_5$, R$_{10}$ and R$_{13}$, independently from each other, are hydrogen, cyano, C$_1$-C$_2$alkyl, C$_3$-C$_6$cycloalkyl, C$_1$-C$_2$haloalkyl, C(O)C$_1$-C$_3$alkyl, (CO)OC$_1$-C$_3$alkyl, SO$_2$NHC$_1$-C$_3$alkyl, SO$_2$N(C$_1$-C$_3$alkyl), SO$_2$C$_1$-C$_3$alkyl, SO$_2$-phenyl, wherein the said phenyl can be mono- or polysubstituted on the phenyl ring by substituents selected from the group consisting of C$_1$-C$_3$alkyl, C$_1$-C$_3$haloalkyl, C$_1$-C$_3$alkoxy, C$_1$-C$_3$haloalkoxy, halogen, cyano and nitro;
R$_6$, R$_7$, R$_8$, R$_9$, R$_{11}$, R$_{12}$, R$_{14}$, R$_{15}$, R$_{16}$ and R$_{17}$, independently from each other, are hydrogen, halogen, nitro, cyano, hydroxy, CHO, C$_1$-C$_6$alkyl, C$_2$-C$_6$alkenyl, C$_2$-C$_6$alkynyl, C$_3$-C$_6$cycloalkyl, C$_1$-C$_6$haloalkyl, C$_2$-C$_6$haloalkenyl, C$_2$-C$_6$haloalkynyl, C$_3$-C$_6$halocycloalkyl, C$_1$-C$_4$alkoxy, C$_1$-C$_4$alkoxy-C$_1$-C$_4$alkoxy-C$_1$-C$_4$alkyl, C$_1$-C$_4$haloalkoxy, C$_1$-C$_4$alkylthio, C$_1$-C$_4$haloalkylthio, C$_1$-C$_4$haloalkylsulfinyl, C$_1$-C$_4$haloalkylsulfonyl, C$_1$-C$_4$alkylsulfinyl, C$_1$-C$_4$alkylsulfonyl, C$_1$-C$_4$alkylsulfonyl-C$_1$-C$_4$alkyl, C$_1$-C$_4$alkylsulfoximino-C$_1$-C$_4$alkyl, C$_1$-C$_4$alkylamino, C$_2$-C$_4$dialkylamino, C$_3$-C$_6$cycloalkylamino, C$_1$-C$_6$alkyl-C$_3$-C$_6$cycloalkylamino, C$_2$-C$_4$alkylcarbonyl, C$_2$-C$_6$alkoxycarbonyl, C$_2$-C$_6$alkylaminocarbonyl, C$_3$-C$_6$dialkylaminocarbonyl, C$_2$-C$_6$alkoxycarbonyloxy, C$_2$-C$_6$alkylaminocarbonyloxy, C$_3$-C$_6$dialkylaminocarbonyloxy, C$_1$-C$_4$alkoxyimino-C$_1$-C$_4$alkyl, —CONHSO$_2$—C$_1$-C$_6$-alkyl, —CONHSO$_2$N(C$_1$-C$_6$-alkyl)$_2$, or are a three- to ten-membered, monocyclic or fused bicyclic ring system which may be aromatic, partially saturated or fully saturated, said three- to ten-membered, monocyclic or fused bicyclic ring system can be substituted by one to three substituents independently selected from the group consisting of C$_1$-C$_4$alkyl, C$_2$-C$_4$alkenyl, C$_2$-C$_4$alkynyl, C$_3$-C$_6$cycloalkyl, C$_1$-C$_4$haloalkyl, C$_2$-C$_4$haloalkenyl, C$_2$-C$_4$haloalkynyl, C$_3$-C$_6$halocycloalkyl, halogen, cyano, nitro, C$_1$-C$_4$alkoxy, C$_1$-C$_4$haloalkoxy, C$_1$-C$_4$alkylthio, C$_1$-C$_4$alkylsulfinyl, C$_1$-C$_4$alkylsulfonyl, C$_1$-C$_4$alkylsulfoximino, C$_1$-C$_4$alkylamino, C$_2$-C$_6$dialkylamino, C$_3$-C$_6$cycloalkylamino, C$_1$-C$_4$alkyl-C$_3$-C$_6$cycloalkylamino, C$_2$-C$_4$alkylcarbonyl, C$_2$-C$_6$alkoxycarbonyl, C$_2$-C$_6$alkylaminocarbonyl, and C$_2$-C$_8$ dialkylaminocarbonyl;
R$_{18}$ and R$_{19}$, independently from each other, are hydrogen, halogen, nitro, cyano, hydroxy, CHO, C$_1$-C$_6$alkyl, C$_2$-C$_6$alkenyl, C$_2$-C$_6$alkynyl, C$_1$-C$_6$alkoxy, C$_3$-C$_6$cycloalkyl, C$_1$-C$_6$haloalkyl, C$_2$-C$_6$haloalkenyl, C$_2$-C$_6$haloalkynyl, C$_3$-C$_6$halocycloalkyl, C$_1$-C$_4$alkylsulfonyl, C$_1$-C$_4$alkylsulfonyl-C$_1$-C$_4$alkyl, C$_2$-C$_4$alkylcarbonyl, C$_2$-C$_6$alkoxycarbonyl, C$_2$-C$_6$alkylaminocarbonyl, C$_3$-C$_6$dialkylaminocarbonyl, C$_2$-C$_6$alkoxycarbonyloxy, C$_2$-C$_6$alkylaminocarbonyloxy, C$_3$-C$_6$dialkylaminocarbonyloxy, C$_1$-C$_4$alkoxyimino-C$_1$-C$_4$alkyl, —CONHSO$_2$—C$_1$-C$_6$-alkyl, —CONHSO$_2$N(C$_1$-C$_6$-alkyl)$_2$, or are a three- to ten-membered, monocyclic or fused bicyclic ring system which may be aromatic, partially saturated or fully saturated, said three- to ten-membered, monocyclic or fused bicyclic ring system can be substituted by one to three substituents independently selected from the group consisting of C$_1$-C$_4$alkyl, C$_2$-C$_4$alkenyl, C$_2$-C$_4$alkynyl, C$_3$-C$_6$cycloalkyl, C$_1$-C$_4$haloalkyl, C$_2$-C$_4$haloalkenyl, C$_2$-C$_4$haloalkynyl, C$_3$-C$_6$halocycloalkyl, halogen, cyano, nitro, C$_1$-C$_4$alkoxy, C$_1$-C$_4$haloalkoxy, C$_1$-C$_4$alkylthio, C$_1$-C$_4$alkylsulfinyl, C$_1$-C$_4$alkylsulfonyl, C$_1$-C$_4$alkylsulfoximino, C$_1$-C$_4$alkylamino, C$_2$-C$_6$dialkylamino, C$_3$-C$_6$cycloalkylamino, C$_1$-C$_4$alkyl-C$_3$-C$_6$cycloalkylamino, C$_2$-C$_4$alkylcarbonyl, C$_2$-C$_6$alkoxycarbonyl, C$_2$-C$_6$alkylaminocarbonyl, and C$_2$-C$_8$ dialkylaminocarbonyl;
Z$_1$ is oxygen, NOR$_{20}$, NR$_{21}$, N—NR$_{22}$R$_{23}$, or N—N(R$_{24}$)SO$_2$(R$_{25}$),
R$_{20}$, R$_{21}$, R$_{22}$ and R$_{25}$ independently from each other, are hydrogen, C$_1$-C$_6$alkyl, C$_2$-C$_6$alkenyl, C$_2$-C$_6$alkynyl, C$_3$-C$_6$cycloalkyl, C$_1$-C$_6$haloalkyl, C$_2$-C$_6$haloalkenyl, C$_2$-C$_6$haloalkynyl, C$_3$-C$_6$halocycloalkyl, C$_1$-C$_6$alkyl- $C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, —CONHSO$_2$—$C_1$-$C_6$-alkyl, —CONHSO$_2$N($C_1$-$C_6$-alkyl)$_2$ or are a five- to ten-membered monocyclic or fused bicyclic ring system which may be aromatic, saturated or partially saturated and may contain 1 to 4 heteroatoms selected from the group consisting of nitrogen, oxygen and sulfur, where the ring system is attached directly or via a $C_1$-$C_4$alkylene, $C_2$-$C_4$alkenyl-$C_1$-$C_4$alkylene, $C_2$-$C_4$alkynyl-$C_1$-$C_4$alkylene, —NH—$C_1$-$C_4$alkylene, —N($C_1$-$C_4$alkyl)$C_1$-$C_4$alkylene, SO—$C_1$-$C_4$alkylene, SO—$C_1$-$C_4$alkylene, —SO$_2$—$C_1$-$C_4$alkylene or O— $C_1$-$C_4$alkylene group to the heteroatom substituent, and where each ring system may not contain more than two oxygen atoms and not more than two sulfur atoms and the ring system for its part may be mono-, di- or trisubstituted by $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, hydroxyl, $C_1$-$C_6$haloalkoxy, $C_3$-$C_6$alkenyloxy, $C_3$-$C_6$alkynyloxy, mercapto, $C_1$-$C_6$alkylthio, $C_1$-$C_6$haloalkylthio, $C_3$-$C_6$alkenylthio, $C_3$-$C_6$haloalkenylthio, $C_3$-$C_6$alkynylthio, $C_2$-$C_5$alkoxyalkylthio, $C_3$-$C_5$acetylalkylthio, $C_3$-$C_6$alkoxycarbonylalkylthio, $C_2$-$C_4$cyanoalkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_2$alkylaminosulfonyl, di($C_1$-$C_2$alkyl)aminosulfonyl, di($C_1$-$C_4$alkyl)amino, halogen, cyano, nitro, phenyl and benzylthio, said phenyl and benzylthio can be mono- or polysubstituted on the phenyl ring by substituents selected from the group consisting of $C_1$-$C_3$alkyl, $C_1$-$C_3$haloalkyl, $C_1$-$C_3$alkoxy, $C_1$-$C_3$haloalkoxy, halogen, cyano and nitro, and where the substituents on the nitrogen in the heterocyclic ring are different from halogen;

$R_{23}$ and $R_{24}$ are hydrogen or $C_1$-$C_3$alkyl;

Q is a ring system $Q_1$

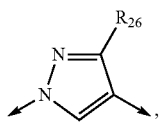
(Q$_1$)

wherein $R_{26}$ is hydrogen, $C_1$-$C_4$alkyl, halogen, $C_1$-$C_4$haloalkyl, cyano, $C_1$-$C_4$alkoxy, hydroxyl, amino, $C_1$-$C_4$alkylamino, di-($C_1$-$C_4$alkyl)amino, $C_1$-$C_4$alkylthio or nitro;

or $R_{26}$ is a three- to four- membered ring system which can be partially saturated or fully saturated and can contain one heteroatom selected form the group consisting of nitrogen, oxygen and sulfur; said three- to four- membered ring system can be mono- to polysubstituted by substituents independently selected from the group consisting of halogen, methyl and trifluoromethyl;

$m_1$ is 0 or 1; and $n_1$ and $n_2$, independently from each other, are 0, 1 or 2; and agrochemically acceptable salts/enantiomers/tautomers/N-oxides of those compounds.

2. A compound of formula I according to claim 1, wherein
$X_1$ is CH or C—F;
$A_1$ is oxygen, S(O)n$_1$, C=O, NR$_5$, CR$_6$R$_7$, —CR$_8$CR$_9$— or a direct bond;
$A_2$ is CR$_{11}$R$_{12}$; and
$A_3$ is CR$_{14}$R$_{15}$ or —CR$_{16}$CR$_{17}$—; and
$R_{26}$ is hydrogen, $C_1$-$C_4$alkyl, halogen, $C_1$-$C_4$haloalkyl, cyano, $C_1$-$C_4$alkoxy, hydroxyl, amino, $C_1$-$C_4$alkylamino, di-($C_1$-$C_4$alkyl)amino, $C_1$-$C_4$alkylthio or nitro.

3. A compound of formula I according to claim 1, wherein
$X_1$ is CH or C—F;
$G_1$ is CR$_2$;
$G_2$ is CR$_3$; or
$G_1$-$G_2$ together is —S—, —O—;
$A_1$ is oxygen, S(O)n$_1$, C=O, NR$_5$, CR$_6$R$_7$, —CR$_8$CR$_9$— or a direct bond;
$A_2$ is CR$_{11}$R$_{12}$;
$A_3$ is CR$_{14}$R$_{15}$ or —CR$_{16}$CR$_{17}$—; and
$R_{26}$ is hydrogen, $C_1$-$C_4$alkyl, halogen, $C_1$-$C_4$haloalkyl, cyano, $C_1$-$C_4$alkoxy, hydroxyl, amino, $C_1$-$C_4$alkylamino, di-($C_1$-$C_4$alkyl)amino, $C_1$-$C_4$alkylthio or nitro.

4. A compound of formula I according to claim 1, wherein
$X_1$ is CH;
$G_1$ is CH;
$G_2$ is CH; or
$G_1$-$G_2$ together is —S—;
$A_1$ is oxygen, S(O)n$_1$, C=O, NR$_5$, CR$_6$R$_7$, —CR$_8$CR$_9$— or a direct bond;
$A_2$ is CR$_{11}$R$_{12}$;
$A_3$ is CR$_{14}$R$_{15}$ or —CR$_{16}$CR$_{17}$—; and
$R_{26}$ is hydrogen, $C_1$-$C_4$alkyl, halogen, $C_1$-$C_4$haloalkyl, cyano, $C_1$-$C_4$alkoxy, hydroxyl, amino, $C_1$-$C_4$alkylamino, di-($C_1$-$C_4$alkyl)amino, $C_1$-$C_4$alkylthio or nitro.

5. A compound of formula I according to claim 1, wherein
$X_1$ is CH;
$G_1$ is CH;
$G_2$ is CH; or
$G_1$-$G_2$ together is —S—;
$A_1$ is oxygen, S(O)n$_1$, C=O, NR$_5$, CR$_6$R$_7$, —CR$_8$CR$_9$— or a direct bond;
$A_2$ is CR$_{11}$R$_{12}$;
$A_3$ is CR$_{14}$R$_{15}$ or —CR$_{16}$CR$_{17}$—;
$R_{26}$ is hydrogen, $C_1$-$C_4$alkyl, halogen, $C_1$-$C_4$haloalkyl, cyano, $C_1$-$C_4$alkoxy, hydroxyl, amino, $C_1$-$C_4$alkylamino, di-($C_1$-$C_4$alkyl)amino, $C_1$-$C_4$alkylthio or nitro; and
$Z_1$ is NOR$_{20}$, N—NR$_{22}$R$_{23}$, or N—N(R$_{24}$)SO$_2$(R$_{25}$).

6. A compound of formula I according to claim 1, wherein
$X_1$ is CH;
$G_1$ is CH;
$G_2$ is CH; or
$G_1$-$G_2$ together is —S—;
$A_1$ is oxygen, S(O)n$_1$, C=O, NR$_5$, CR$_6$R$_7$, —CR$_8$CR$_9$— or a direct bond;
$A_2$ is CH$_2$;
$A_3$ is CH$_2$ or —CH$_2$CH$_2$—;
$R_{26}$ is hydrogen, $C_1$-$C_4$alkyl, halogen, $C_1$-$C_4$haloalkyl, cyano, $C_1$-$C_4$alkoxy, hydroxyl, amino, $C_1$-$C_4$alkylamino, di-($C_1$-$C_4$alkyl)amino, $C_1$-$C_4$alkylthio or nitro; and
$Z_1$ is NOR$_{20}$, N—NR$_{22}$R$_{23}$, or N—N(R$_{24}$)SO$_2$(R$_{25}$).

7. A compound of formula I according to claim 1, wherein
$X_1$ is CH;
$G_1$ is CH;
$G_2$ is CH;
$A_1$ is oxygen, S(O)n$_1$, C=O, NR$_5$, CH$_2$, —CH$_2$CH$_2$— or a direct bond;
$A_2$ is CH$_2$;

$A_3$ is $CH_2$ or $-CH_2CH_2-$;

$R_{26}$ is hydrogen, $C_1$-$C_4$alkyl, halogen, $C_1$-$C_4$haloalkyl, cyano, $C_1$-$C_4$alkoxy, hydroxyl, amino, $C_1$-$C_4$alkylamino, di-($C_1$-$C_4$alkyl)amino, $C_1$-$C_4$alkylthio or nitro; and $Z_1$ is $NOR_{20}$, $N-NR_{22}R_{23}$, or $N-N(R_{24})SO_2(R_{25})$.

8. A compound of formula I according to claim 1, wherein $X_1$ is CH;

$G_1$ is CH;

$G_2$ is CH; or $G_1$-$G_2$ together is $-S-$;

$A_1$ is oxygen, $S(O)n_1$, $C=O$, $NR_5$, $CH_2$, $-CH_2CH_2-$ or a direct bond;

$A_2$ is $CH_2$;

$A_3$ is $CH_2$;

$R_{26}$ is hydrogen, $C_1$-$C_4$alkyl, halogen, $C_1$-$C_4$haloalkyl, cyano, $C_1$-$C_4$alkoxy, hydroxyl, amino, $C_1$-$C_4$alkylamino, di-($C_1$-$C_4$alkyl)amino, $C_1$-$C_4$alkylthio or nitro; and $Z_1$ is $NOR_{20}$.

9. A compound of formula I according to claim 1, wherein $X_1$ is CH;

$G_1$ is CH;

$G_2$ is CH;

$A_1$ is oxygen, $S(O)n_1$, $NR_5$, $CH_2$ or a direct bond;

$A_2$ is $CH_2$;

$A_3$ is $CH_2$;

$R_{26}$ is hydrogen, $C_1$-$C_4$alkyl, halogen, $C_1$-$C_4$haloalkyl, cyano, $C_1$-$C_4$alkoxy, hydroxyl, amino, $C_1$-$C_4$alkylamino, di-($C_1$-$C_4$alkyl)amino, $C_1$-$C_4$alkylthio or nitro; and $Z_1$ is $NOR_{20}$, $N-NR_{22}R_{23}$, or $N-N(R_{24})SO_2(R_{25})$.

10. A pesticidal composition, which comprises at least one compound of formula I according to claim 1 or, where appropriate, a tautomer thereof, in each case in free form or in agrochemically utilizable salt form, as active ingredient and at least one auxiliary.

11. A method for controlling pests, which comprises applying a composition according to claim 5 to the pests or their environment with the exception of a method for treatment of a human or animal body by surgery or therapy and diagnostic methods practised on the human or animal body.

12. A method for the protection of plant propagation material from attack by pests, which comprises treating the propagation material or a site, where the propagation material is planted, with a composition according to claim 10.

13. Plant propagation material treated in accordance with the method described in claim 12.

* * * * *